(12) United States Patent
Mizusawa et al.

(10) Patent No.: US 12,140,549 B2
(45) Date of Patent: Nov. 12, 2024

(54) POLYMER DYE FOR DETECTING HYDROGEN PEROXIDE AND STRUCTURE FOR DETECTING HYDROGEN PEROXIDE

(71) Applicant: CANON KABUSHIKI KAISHA, Tokyo (JP)

(72) Inventors: Keigo Mizusawa, Kanagawa (JP); Ryuji Higashi, Kanagawa (JP); Masanori Seki, Kanagawa (JP); Takeshi Yamamoto, Kanagawa (JP); Kengo Kanazaki, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 939 days.

(21) Appl. No.: 17/109,565

(22) Filed: Dec. 2, 2020

(65) Prior Publication Data

US 2021/0096081 A1   Apr. 1, 2021

Related U.S. Application Data

(63) Continuation of application No. PCT/JP2019/022577, filed on Jun. 6, 2019.

(30) Foreign Application Priority Data

Jun. 7, 2018   (JP) .................. 2018-109803

(51) Int. Cl.
*G01N 21/78*   (2006.01)
*C07F 5/04*    (2006.01)
*C08K 3/38*    (2006.01)
*C09B 69/10*   (2006.01)
*G01N 33/52*   (2006.01)

(52) U.S. Cl.
CPC ............... *G01N 21/78* (2013.01); *C07F 5/04* (2013.01); *C08K 3/38* (2013.01); *C09B 69/109* (2013.01); *G01N 33/523* (2013.01)

(58) Field of Classification Search
CPC ........ G01N 21/78; G01N 33/523; C08K 3/38; C09B 69/109
See application file for complete search history.

(56) References Cited

U.S. PATENT DOCUMENTS

| | | | |
|---|---|---|---|
| 4,613,465 A | 9/1986 | Yamanishi et al. | |
| 4,670,385 A | 6/1987 | Babb et al. | |
| 4,673,635 A | 6/1987 | Yamanishi et al. | |
| 4,778,753 A | 10/1988 | Yamanishi et al. | |
| 4,810,642 A | 3/1989 | Aoyama et al. | |
| 4,868,130 A * | 9/1989 | Hargreaves | G01N 33/537 436/526 |
| 5,108,502 A * | 4/1992 | Pawlowski | C09B 31/072 347/100 |
| 6,277,750 B1 | 8/2001 | Pawlowski et al. | |
| 6,919,463 B2 * | 7/2005 | Akhavan-Tafti | C07F 5/025 549/213 |
| 6,927,246 B2 * | 8/2005 | Noronha | C07F 5/025 436/95 |
| 8,137,990 B2 * | 3/2012 | Akhavan-Tafti | C07F 5/025 549/213 |

(Continued)

FOREIGN PATENT DOCUMENTS

| JP | 56-026199 A | 3/1981 |
|---|---|---|
| JP | 56-031641 A | 3/1981 |

(Continued)

OTHER PUBLICATIONS

Nishiyabu et al. "Surface modification of a polyvinyl alcohol sponge with functionalized boronic acids to develop porous materials for multicolor emission, chemical sensing and 3D cell culture", ChemComm, 2017, 53, 3563. Published online Mar. 6, 2017 (Year: 2017).*

(Continued)

*Primary Examiner* — Jane L Stanley

(74) *Attorney, Agent, or Firm* — Venable LLP

(57) ABSTRACT

A polymer dye includes at least one repeating unit represented by the following structural formula 1 and at least one selected from the group consisting of repeating units represented by the following structural formulas 2 and 3:

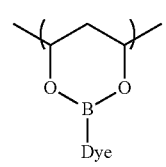

Structural Formula 1

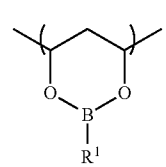

Structural Formula 2

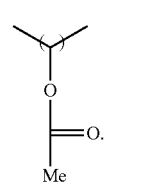

Structural Formula 3

Hydrogen peroxide present in or generated through enzymatic reaction in a biological sample can be detected by using the polymer dye.

3 Claims, 1 Drawing Sheet

(56) References Cited

U.S. PATENT DOCUMENTS

| | | | | |
|---|---|---|---|---|
| 2008/0057528 | A1* | 3/2008 | Sayre | G01N 33/523 435/27 |
| 2008/0099172 | A1* | 5/2008 | Pelton | C08F 226/02 162/164.6 |
| 2008/0160225 | A1* | 7/2008 | Lowe | G01N 33/5308 564/207 |
| 2018/0243442 | A1* | 8/2018 | Lam | A61K 9/5138 |

FOREIGN PATENT DOCUMENTS

| | | |
|---|---|---|
| JP | 60-194363 A | 10/1985 |
| JP | 60-256056 A | 12/1985 |
| JP | 62-296 A | 1/1987 |
| JP | 62-093261 A | 4/1987 |
| JP | 3-206896 A | 9/1991 |
| JP | 2006-520465 A | 9/2006 |
| WO | 2000/03303 A1 | 1/2000 |
| WO | 2004/074810 | 9/2004 |
| WO | 2019/235579 A1 | 12/2019 |

OTHER PUBLICATIONS

Nishiyabu et al. "Boronic acids as molecular inks for surface functionalization of polyvinyl alcohol substrates", New J. Chem., 2018, 42, 7392. Published online Mar. 29, 2018 (Year: 2018).*

Nishiyabu et al. "Dansyl-containing boronate hydrogel film as fluorescent chemosensor of copper ions in water", RSC Advances, 2012, 2, 6555-6561. Published May 14, 2012. (Year: 2012).*

De Luscancay et al. "Temperature-controlled release of catechol dye in thermosensitive phenylboronate-containing copolymers: a quantitative study", European Polymer Journal, 46, 2010, 1367-1373. Published online Apr. 1, 2010. (Year: 2010).*

Nakahashi et al. "Distinct color changes in hydrogen peroxide-responsive thin films consisting of boronic acid-containing polymers", Dyes and Pigments, 218, 2023, 111450. Published online Jun. 5, 2023. (Year: 2023).*

Sato et al. "H2O2-induced decomposition of layer-by-layer films consisting of phenylboronic acid-bearing poly(allylamine) and poly(vinyl alcohol)", Langmuir, 2014, 30, 9247-9250. Published online Jul. 28, 2014. (Year: 2014).*

Takayoshi et al. "Multicolor saccharide-sensing chips created via layer-by-layer adsorption of boronic acid-containing polymers", Sensors and Actuators B, 192, 2014, 776-781. Published online Nov. 11, 2013. (Year: 2013).*

Takeshima et al "Ratiometric sensing of hydrogen peroxide utilizing conformational change in fluorescent boronic acid polymers", Journal of Analytical Methods in Chemistry, vol. 2017, 7pages, ID 7829438. Published Sep. 28, 2017. (Year: 2017).*

Ashish Kulkarni et al., "Reporter Nanoparticle that Monitors its Anticancer Efficacy in Real Time," 113(15) PNAS E2104-E2113 with Supporting Information pp. 1-7 (Mar. 2016).

International Preliminary Report on Patentability in International Application No. PCT/JP2019/022577 (Dec. 2020).

Ryuhei Nishiyabu et al., "Boronic Acid as an Efficient Anchor Group for Surface Modification of Solid Polyvinyl Alcohol," 52(63) Chem. Commun. 9765-9768 (Jul. 2016).

Notice of Reasons for Refusal in Japanese Application No. 2019-104770 (Jul. 2023).

Haruto Wakabayashi et al., Supplementary Information, pp. 1-11, for "Affinity Labeling-Based Introduction of a Reactive Handle for Natural Protein Modification," 3(7) Chemistry—An Asian Journal 1134-1139 (2008).

Alexander R. Lippert et al., "Boronate Oxidation as a Bioorthogonal Reaction Approach for Studying the Chemistry of Hydrogen Peroxide in Living Systems," 44(9) Acc. Chem. Res. 793-804 (Sep. 2011).

Ryuhei Nishiyabu et al., "Boronic Acid as an Efficient Anchor Group for Surface Modification of Solid Polyvinyl Alcohol," 52 Chem. Commun. 9765-9768 (Jun. 2016).

Katsuhiko Sato et al., "Loading and Release of Fluorescent Dye from Layer-by-Layer Film-Coated Magnetic Particles in Response to Hydrogen Peroxide," 432 J Colloid. Interf. Sci. 92-97 (Jul. 2014).

Ashish Kulkarni et al., "Reporter Nanoparticle that Monitors its Anticancer Efficacy in Real Time," 113(15) PNAS E2104-E2113 (Mar. 2016).

Raychelle M. Burks et al., "Current Trends in the Detection of Peroxide-Based Explosives," 395 Anal. Bioanal. Chem. 301-313 (Jul. 2009).

International Search Report in International Application No. PCT/JP2019/022577 (Aug. 2019).

* cited by examiner

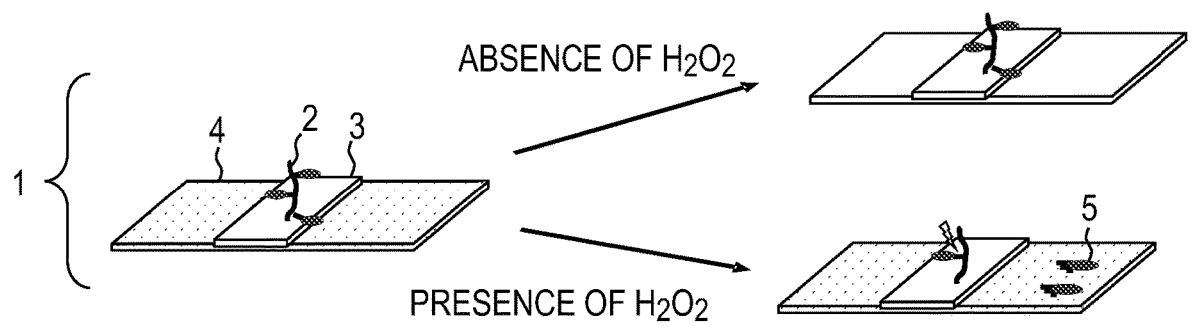

POLYMER DYE FOR DETECTING HYDROGEN PEROXIDE AND STRUCTURE FOR DETECTING HYDROGEN PEROXIDE

CROSS-REFERENCE TO RELATED APPLICATIONS

This application is a Continuation of International Patent Application No. PCT/JP2019/022577, filed Jun. 6, 2019, which claims the benefit of Japanese Patent Application No. 2018-109803, filed Jun. 7, 2018, both of which are hereby incorporated by reference herein in their entirety.

BACKGROUND OF THE INVENTION

Field of the Invention

The present invention relates to a polymer dye capable of quantitatively detecting hydrogen peroxide ($H_2O_2$) specifically in an aqueous sample with high sensitivity, and further relates to a structure for detecting hydrogen peroxide.

Description of the Related Art

Regarding the detection of hydrogen peroxide, there is a demand not only for the detection of hydrogen peroxide itself but also for the detection of hydrogen peroxide as a product of an enzymatic reaction. For example, glucose, uric acid, cholesterol, creatinine, or the like is caused to react with its specific enzyme such as oxidase, and can be detected or quantified based on the amount of hydrogen peroxide generated. In such cases, it is necessary to detect or quantify hydrogen peroxide.

Regarding substances for detecting hydrogen peroxide, there is a case of using an enzyme such as oxidase or peroxidase, a case of using a functional dye that undergoes a detectable color change (absorption or luminescence) in the presence of hydrogen peroxide, or a case of using a combination of them. Typical functional dyes are an oxidizable coloring reagent which is a combination of 4-aminoantipyrine with a phenolic compound or aniline compound, a combination reagent of 3-methyl-2-benzothiazolin hydrazone and an aniline compound, 2,2'-azinobis(3-ethylbenzothiazolin-6-sulfonic acid), a triarylmethane dye, a benzozine derivative, an o-triazine derivative, o-phenylenediamine, and the like. Among them, the triarylmethane dye is known to be useful because the triarylmethane dye achieves very high visibility having a maximum absorption wavelength of around 650 nm, which little overlaps with the absorption wavelength region of hemoglobin, and a molecular extinction coefficient of around $10^5$ (Japanese Patent Application Laid-Open Nos. S56-26199, S56-31641, S60-194363, S60-256056, S62-296, S62-93261, and H03-206896).

Research on devices using dyes that detect hydrogen peroxide has been actively conducted in recent years (Raychelle M. Burks et al., Anal. Bioanal. Chem. 2009, 395, 301-313). For the purpose of detecting metabolites in biological samples, the present inventors examined whether hydrogen peroxide can be detected in the presence of protein (such as albumin) impurities. As a result, the present inventors found that stable detection of hydrogen peroxide was difficult even by use of a highly-sensitive functional dye because the dye was adsorbed on the impurities and was separated and eluted from the device surface, and considered that there is need for a method of immobilizing the dye on a solid surface in order to suppress separation and elution.

In recent years, regarding the immobilization of dyes, a method of immobilizing a fluorescent dye on the surfaces of fine particles by boronic ester bonds has been studied (Katsuhiko Sato et al., J. Colloid. Interface. Sci. 2014, 432, 92-97, Ryuhei Nishiyabu et al., Chem. Commun. 2016, 52, 9765-9768), and inspection devices for detecting the amount of hydrogen peroxide have been reported. However, in our studies, by simply immobilizing a dye on the surfaces of resin particles by boronic ester bonds, it was difficult to suppress the separation and elution of the dye from the resin particles due to adsorption to the impurities and difficult to stably detect hydrogen peroxide. Therefore, we came to the recognition that simple bonding of the dye to the solid surface is insufficient to provide detectors that stably detect hydrogen peroxide.

The present invention has an object to detect hydrogen peroxide present in a biological sample (or generated in a biological sample by an enzymatic reaction).

SUMMARY OF THE INVENTION

In order to achieve the above object, we completed a polymer dye capable of detecting hydrogen peroxide even in the presence of impurities such as protein. Moreover, we completed a structure for detecting hydrogen peroxide using the polymer dye.

The present invention provides a polymer dye including at least one repeating unit represented by the following structural formula 1 and including at least one selected from the group consisting of repeating units represented by the following structural formulas 2 and 3, and provides a structure for detecting hydrogen peroxide including the polymer dye:

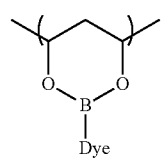

Structural Formula 1

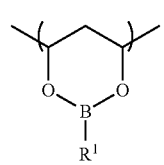

Structural Formula 2

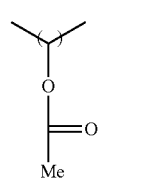

Structural Formula 3

(where Dye in the structural formula 1 is a light absorbing material which contains an ionic or nonionic functional group and in which the maximum value of a molar extinction coefficient at a wavelength of 400 nm to 700 nm is $10^4$ $M^{-1}$ $cm^{-1}$ or more, and $R^1$ in the structural formula 2 is a hydrocarbon chain having 1 to 8 carbon atoms or a substituted or unsubstituted aromatic group).

Further features of the present invention will become apparent from the following description of exemplary embodiments with reference to the attached drawing.

BRIEF DESCRIPTION OF THE DRAWINGS

FIGURE illustrates a structure for detecting hydrogen peroxide as a third embodiment of the present invention.

DESCRIPTION OF THE EMBODIMENTS

As a first embodiment of the present invention, provided is a polymer dye including at least one repeating unit represented by the following structural formula 1 and including any one of repeating units represented by the following structural formulas 2 and 3.

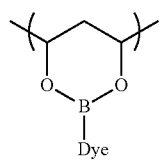

Structural Formula 1

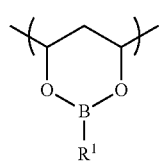

Structural Formula 2

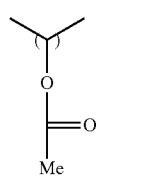

Structural Formula 3

Here, Dye in the structural formula 1 is a light absorbing material which contains an ionic or nonionic functional group and in which the maximum value of a molar extinction coefficient at a wavelength of 400 nm to 700 nm is $10^4 M^{-1} cm^{-1}$ or more.

Then, le in the structural formula 2 is a hydrocarbon chain having 1 to 8 carbon atoms or a substituted or unsubstituted aromatic group.

The polymer dye in the present embodiment is preferably used for detecting hydrogen peroxide. That is, as a second embodiment of the present invention, provided is a polymer dye for detecting hydrogen peroxide containing the polymer dye according to the first embodiment of the present invention.

In the present embodiment, Dye means any of colorants, pigments, fluorescent substances, dyes, gold nanoparticles, gold colloids, silver nanoparticles, and the like each having an ionic or nonionic functional group. In sum, Dye only has to have a molecular structure that is water soluble or water dispersible and is optically measurable or observable.

In the present embodiment, a stability rate of Dye means a color retention rate of Dye against impurities other than hydrogen peroxide in a biological sample. The color retention rate of Dye means a ratio between an absorbance (A0) (derived from Dye for light having a wavelength of a wavelength of 400 nm to 700 nm) measured immediately after addition of Dye to a reference biological sample, and an absorbance (A) measured in the same way after a lapse of a certain period of time (100×A/A0). In the embodiment of the present invention, Dye having a stability rate of 10% or more is preferable from the viewpoint of measurement or the like of an amount of free or non-free Dye after contact and reaction with a biological sample.

A water solubility of Dye is preferably 0.1 mM or more for the following reason. In the polymer dye in the embodiment of the present invention, the boronic ester is cleaved by hydrogen peroxide and Dye is separated from the polymer dye, based on which the presence or absence of hydrogen peroxide is detected. If the water solubility of Dye is 0.1 mM or more, the free Dye cleaved by the decomposition of the boronic ester bond can be transferred into the solution without being re-adsorbed on a base material or the like, and therefore it is easy to measure an optical change of the base material or the amount of Dye transferred.

Dye preferably absorbs visible light, more preferably has a feature of absorbing light with a wavelength of 400 nm to 700 nm, and even more preferably has a feature of absorbing light with a wavelength of 500 nm to 700 nm. The range of absorption wavelength by impurities such as proteins, vitamins, and bilirubin contained in biological samples such as serum and urine is a wavelength of 500 nm or less. When Dye has the aforementioned absorption property, the detection of Dye is less susceptible to impurities and therefore can be achieved with high sensitivity.

In addition, from the viewpoint of easiness of visual observation, Dye is preferably a light absorbing material in which the maximum value of the molar extinction coefficient of Dye is $10^4 M^{-1} cm^{-1}$ or more.

For example, examples of Dye include triarylmethane dyes, azo dyes, xanthene dyes, squarylium dyes, cyanine dyes, gold nanoparticles, gold colloids, silver nanoparticles, and so on. Dye is preferably at least one selected from the group consisting of triarylmethane dyes, azo dyes, xanthene dyes, squarylium dyes, and cyanine dyes. Among them, from the viewpoint of the molar extinction coefficient (ε), Dye is preferably a triarylmethane dye, a xanthene dye, a cyanine dye, or gold nanoparticles having a high ε, and is particularly preferably a xanthene dye. In addition, the structural formula 1 is preferably represented by the following structural formula 7.

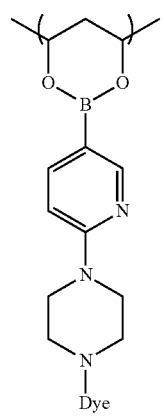

Structural Formula 7

Hereinafter, specific examples of a preferable structure of Dye in the structural formula 1 usable in the present embodiment are presented, but the structure is not limited to the following examples. Here,  indicates the position B in the structural formula 1. In other words,  represents a bond to B of —O—B—O— in the structural formula 1. The same applies to the meaning of ** in the following description.

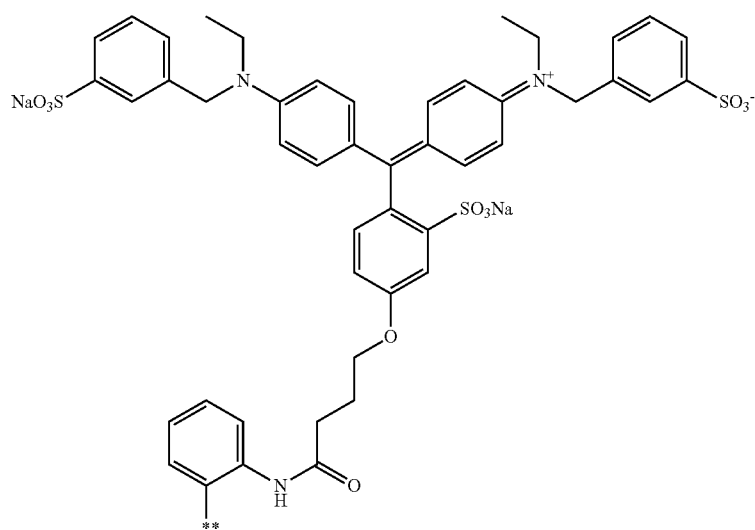
I-I
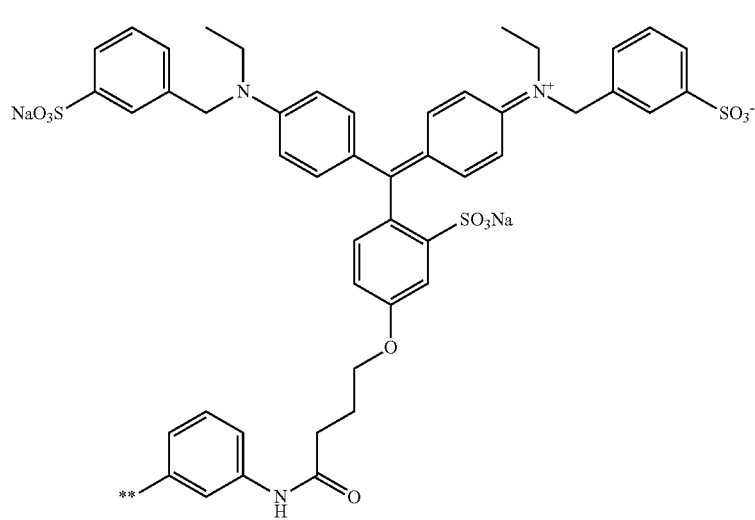
I-II
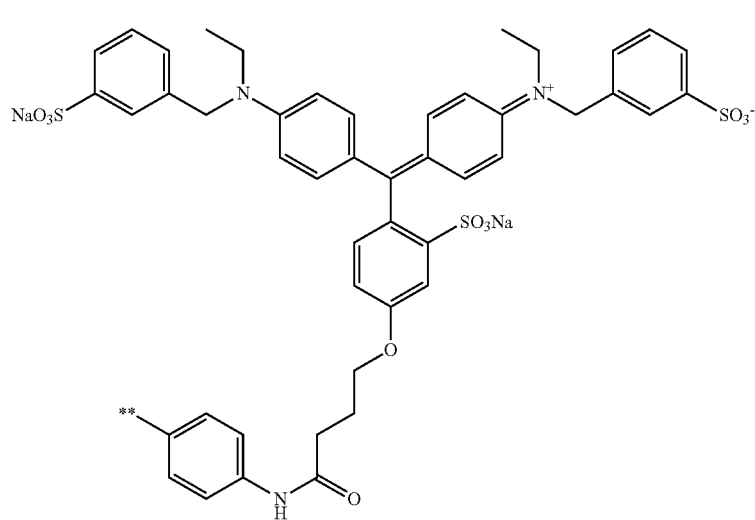
I-III

I-IV
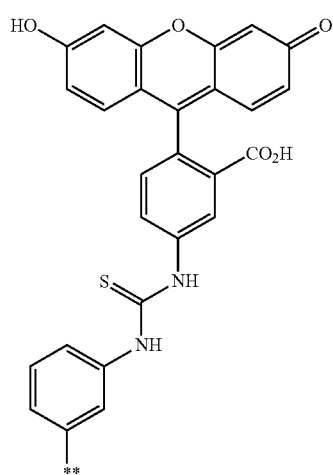
I-V
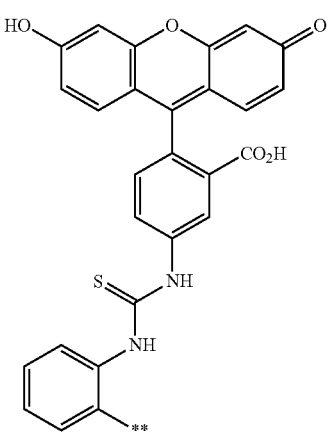
I-VI
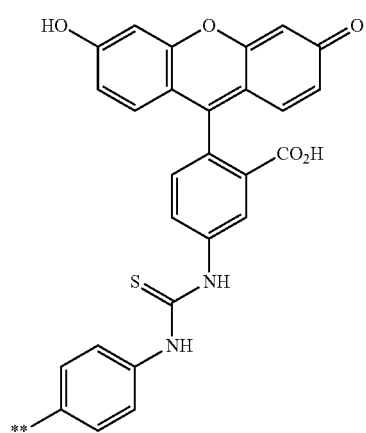
I-VII
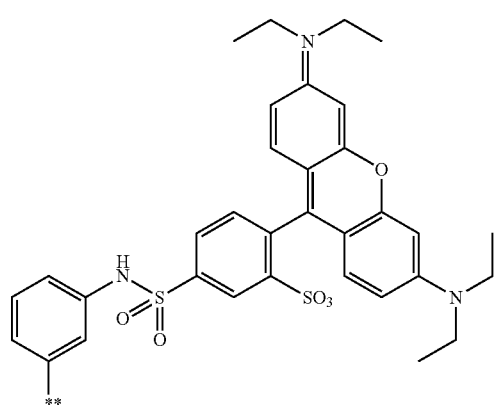
I-VIII
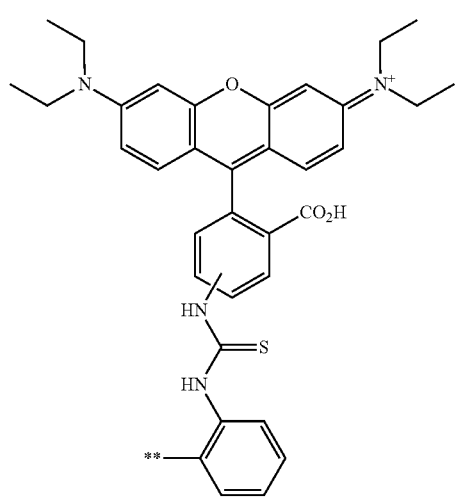
I-IX
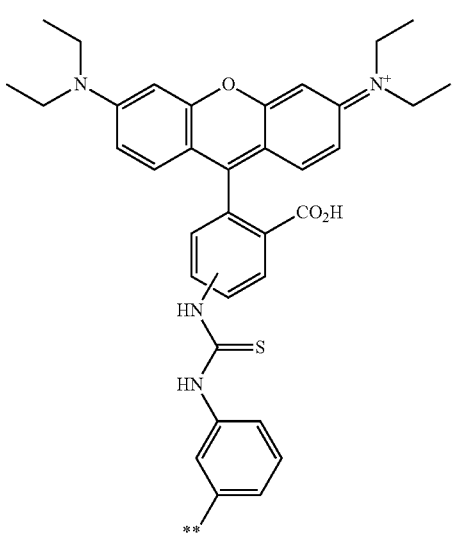

-continued
I-X
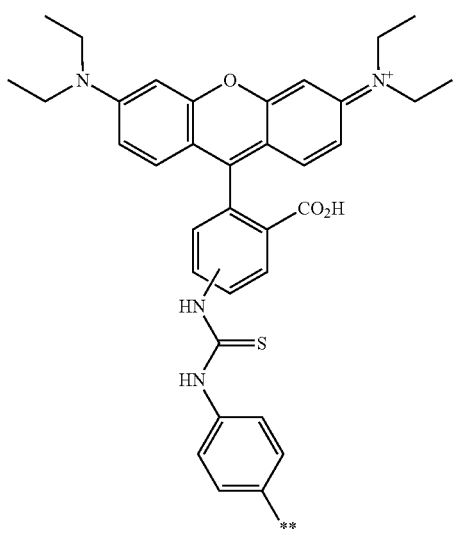
I-XI
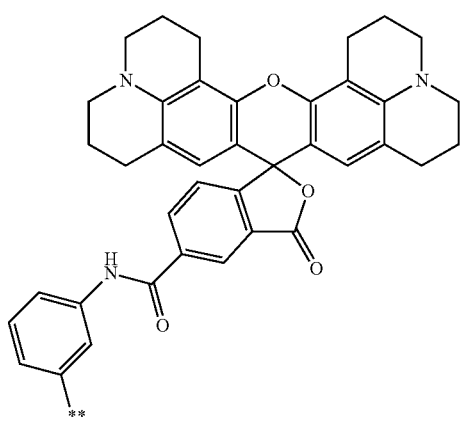
I-XII
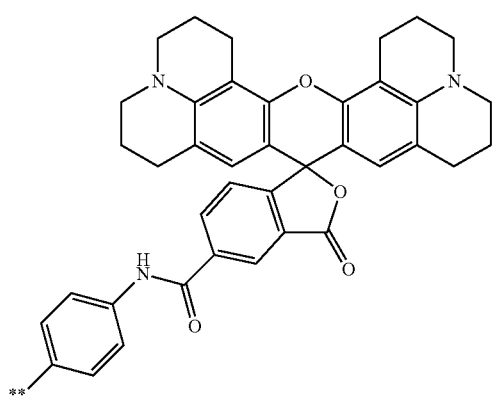
I-XIII
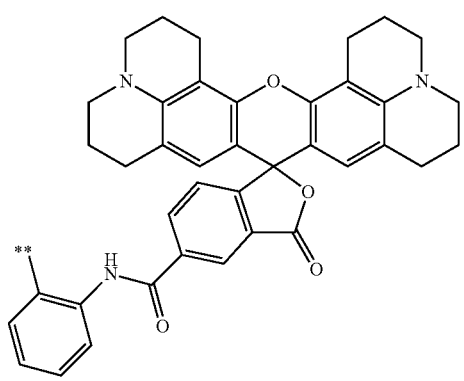
I-XIV
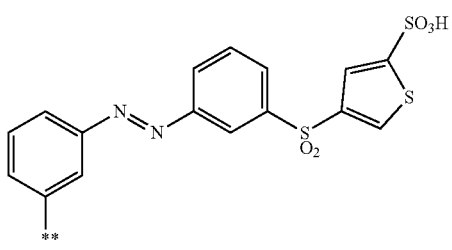
I-XV
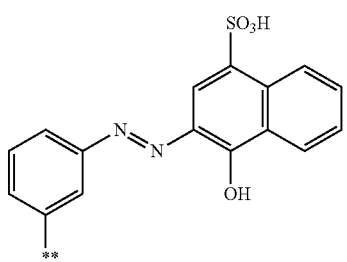
I-XVI
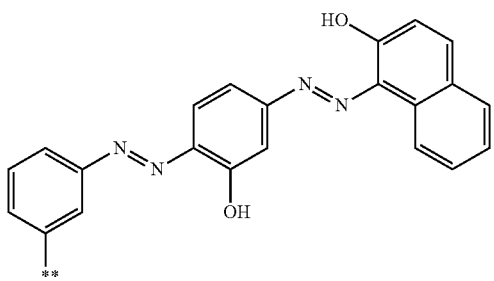
I-XVII
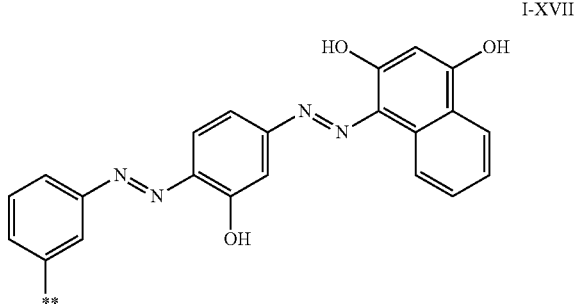

-continued
I-XVIII
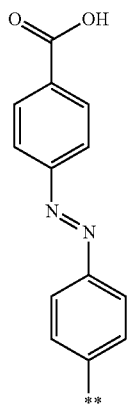
I-XIX
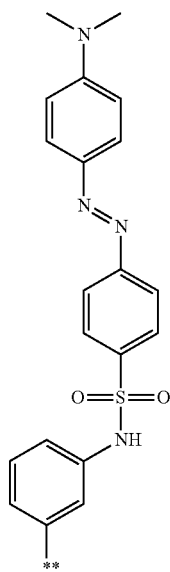
I-XX
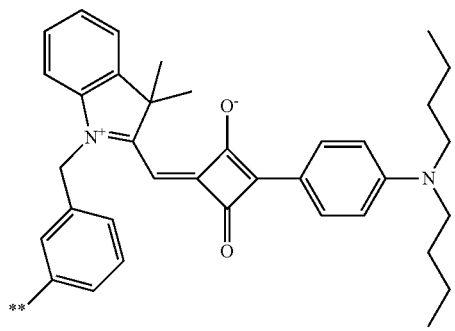
I-XXI
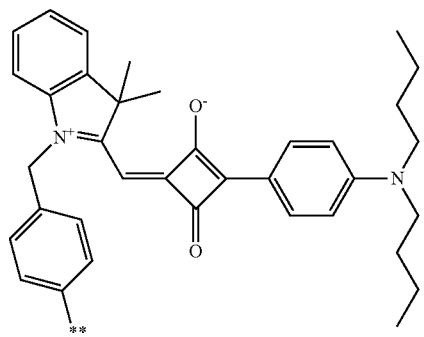
I-XXII
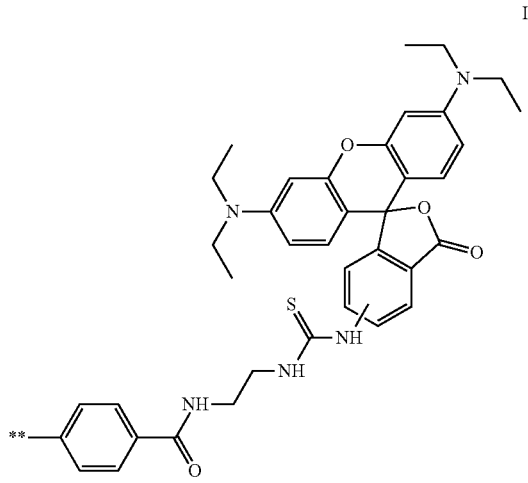
I-XXIII
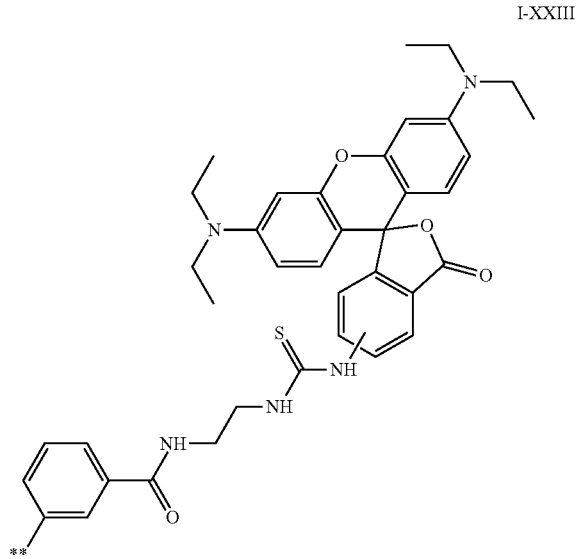

-continued
I-XXIV
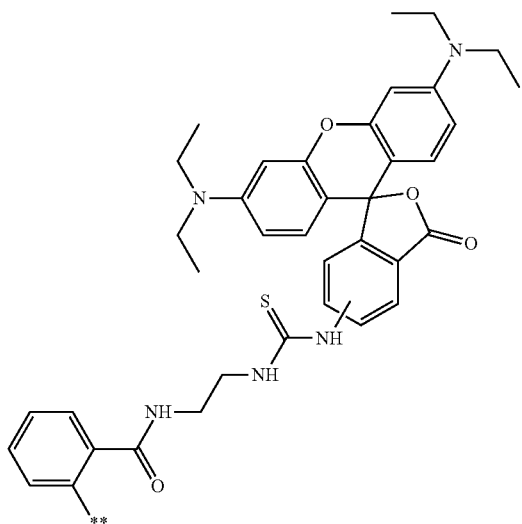
I-XXV
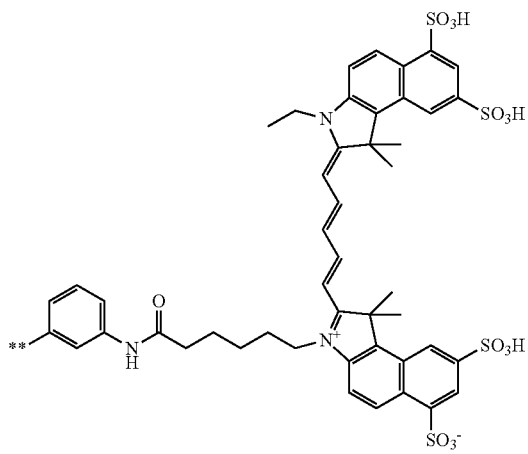
I-XXVI
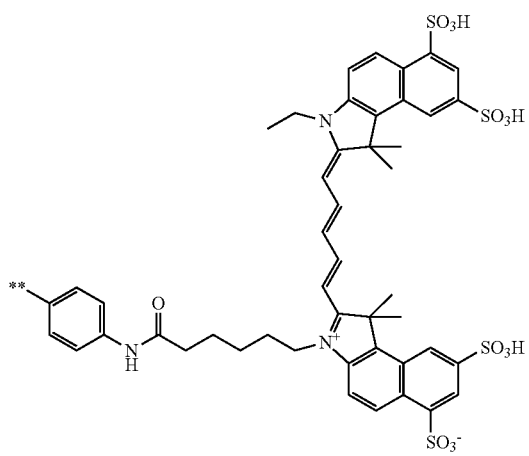
I-XXVII
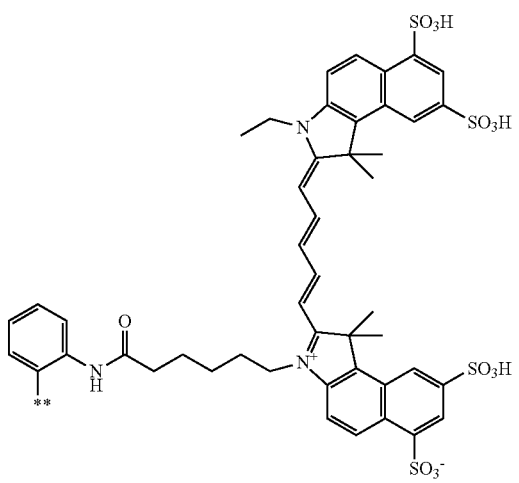
I-XXVIII
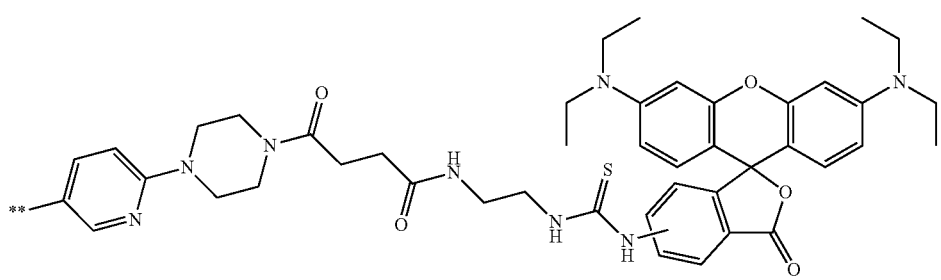
I-XXIX
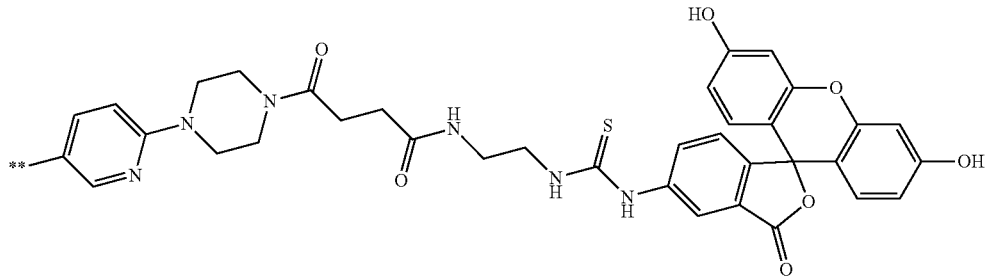

As described above, $R^1$ in the structural formula 2 is a hydrocarbon chain having 1 to 8 carbon atoms or a substituted or unsubstituted aromatic group. In the present embodiment, the hydrocarbon chain means an acyclic or cyclic group formed of non-aromatic (aliphatic) hydrocarbon which may contain a linear or branched structure and may be substituted with a nitro group, a halogen atom, or the like. In the present embodiment, the aliphatic hydrocarbon may be any of saturated aliphatic hydrocarbon and unsaturated aliphatic hydrocarbon.

As examples of the substituted or unsubstituted aromatic group there are aromatic groups represented by the following structural formulas (I) to (IX).

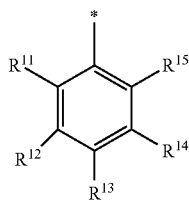
(I)

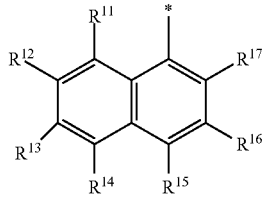
(II)

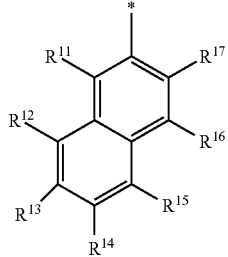
(III)

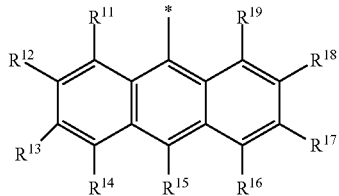
(IV)

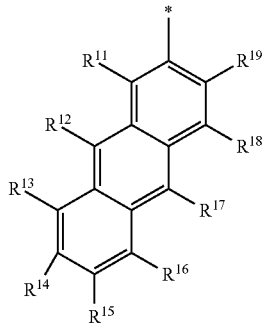
(V)

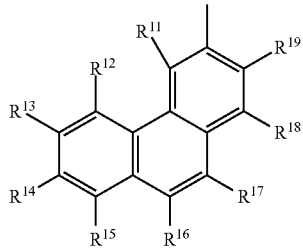
(VI)

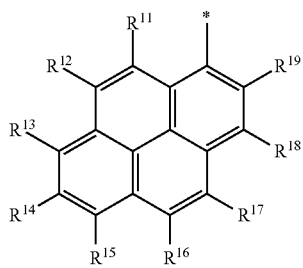
(VII)

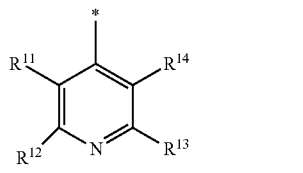
(VIII)

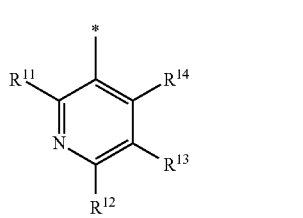
(IX)

In the above formulas (I) to (IX), $R^{11}$ to $R^{19}$ each independently represent any one of a hydrogen atom, a halogen atom, an acetoxy group, an alkyl group having 1 to 8 carbon atoms, an alkoxy carbonyl group having 1 to 8 carbon atoms (RO—CO—), an alkylcarbonyloxy group having 1 to 8 carbon atoms (R—CO—O), a alkyl aminocarbonyl group having 1 to 8 carbon atoms (R—NH—CO—), and an alkylcarbonyl amino group having 1 to 8 carbon atoms (R—CO—NH—). Here, $R^{11}$ to $R^{19}$ are particularly preferably hydrogen atoms. Here, * indicates the position B in the structural formula 2. In other words, * represents a bond to B of —O—B—O— in the structural formula 2. The same applies to the meaning of * in the following description.

As an example of a method for producing a polymer dye in the present embodiment, there is a method including mixing and bonding a resin such as polyvinyl alcohol (which may be abbreviated as PVA) or a butyral resin with and to a boronic acid-containing dye as illustrated in the following formulas 1-1 to 1-29. Through this method, the polymer to which the dye is bonded by the boronic ester bond can be obtained.

Regarding polyvinyl alcohol or the like as a raw material, the weight average molecular weight and the degree of saponification are not particularly limited, but the degree of saponification is preferably 65 mol % or more and more preferably 70 mol % or more. Here, the degree of saponification is a ratio of the number of moles of hydroxyl groups generated by a saponification reaction for saponifying polyvinyl acetate to obtain polyvinyl alcohol, and the value measured by the method in accordance with JIS-K6726 is used. When the degree of saponification is low, the amount of the structural formula 1 obtained is small, so that the color development property tends to decrease. In addition, when the degree of saponification is low, the amount of structural formula 2 obtained is also small, so that the polymer dye tends to be dissolved. The weight average molecular weight is preferably 5000 to 186000, both inclusive, and more preferably 9000 to 124000, both inclusive. When the weight average molecular weight is small, the polymer dye has high water solubility, so that the polymer dye hardly interacts hydrophobically with the base material, and is scarcely bonded to the base material. When the weight average molecular weight is large, the polymer dye has low water solubility. In this case, in the presence of hydrogen peroxide, the polymer dye is hardly separated from a base material and causes a variation of a color change on the base material, so that the detection accuracy tends to decrease.

Specific examples of a boronic acid-containing dye usable in the method for producing the polymer dye in the embodiment are presented below, but the dye is not limited to the following structures.

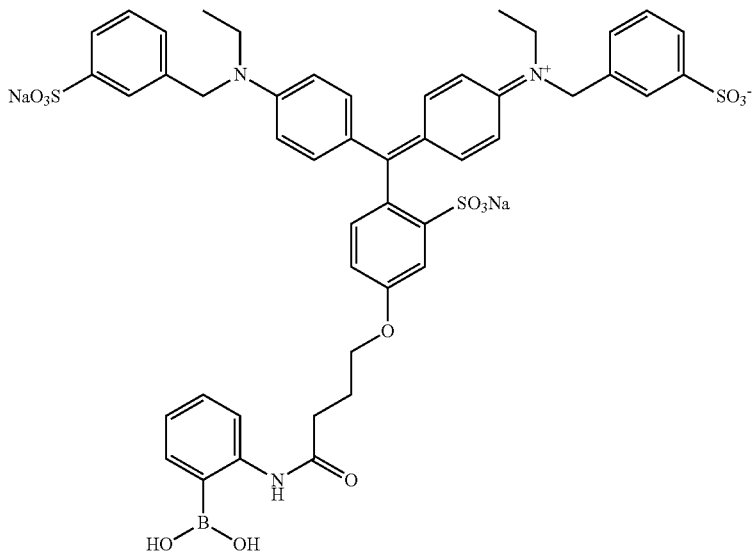

1-1

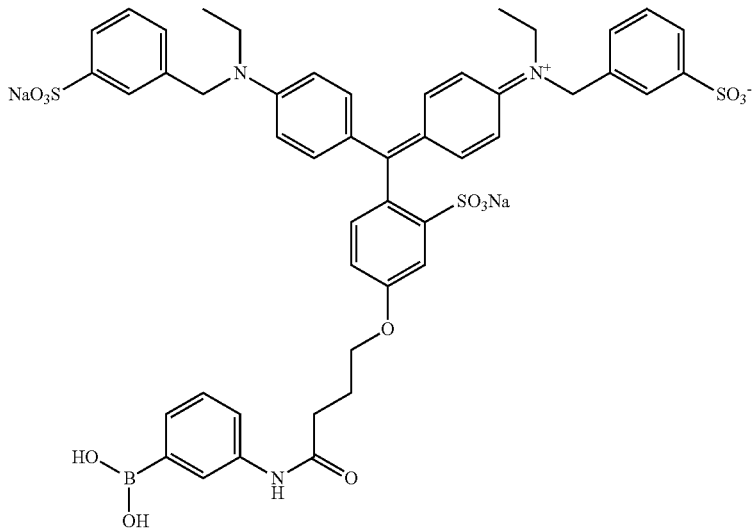

1-2

-continued
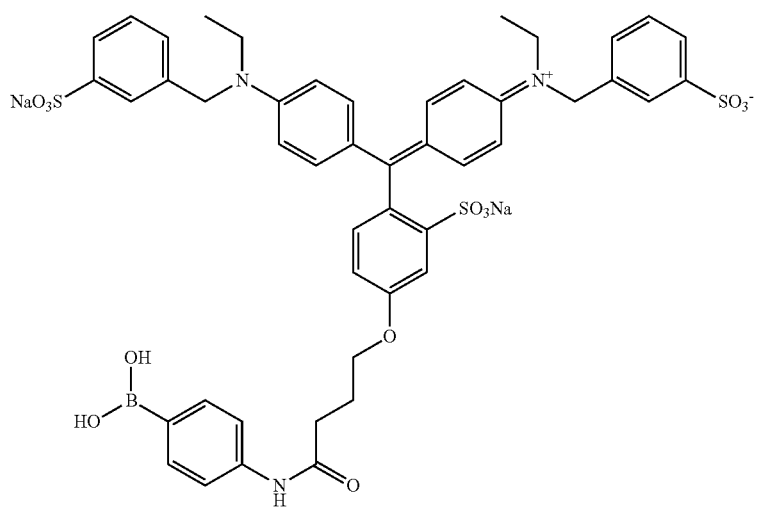
1-3
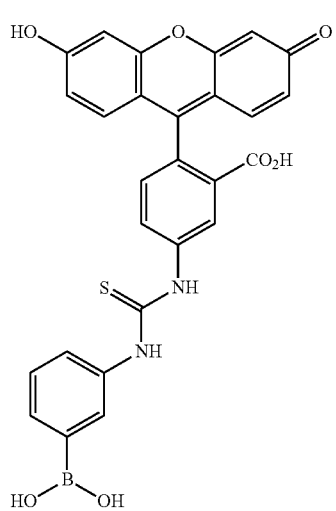
1-4
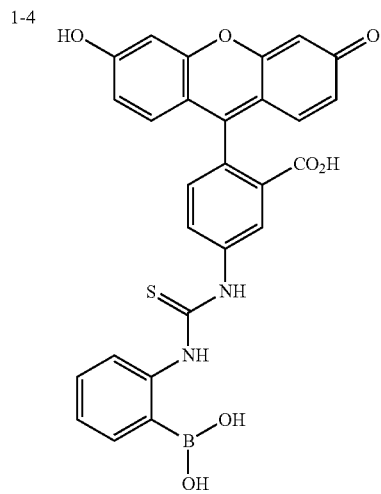
1-5
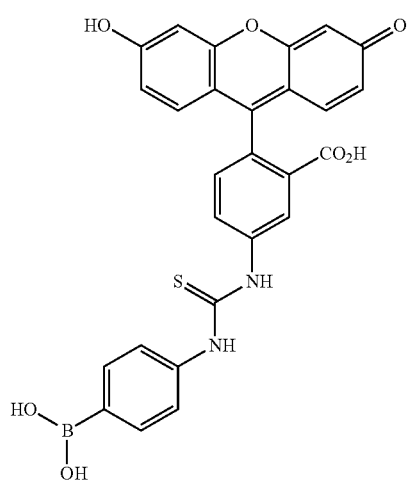
1-6
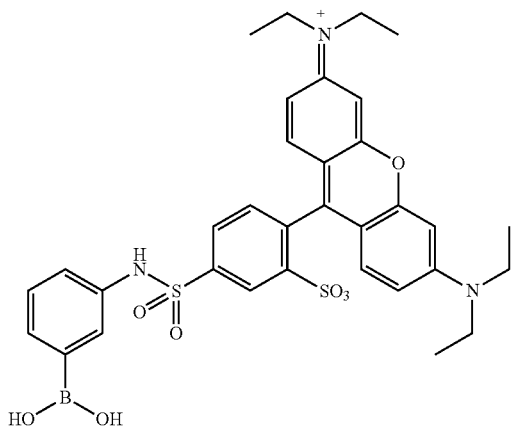
1-7

-continued
1-8
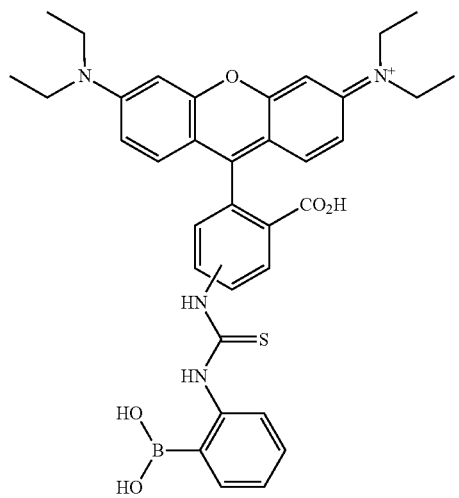
1-9
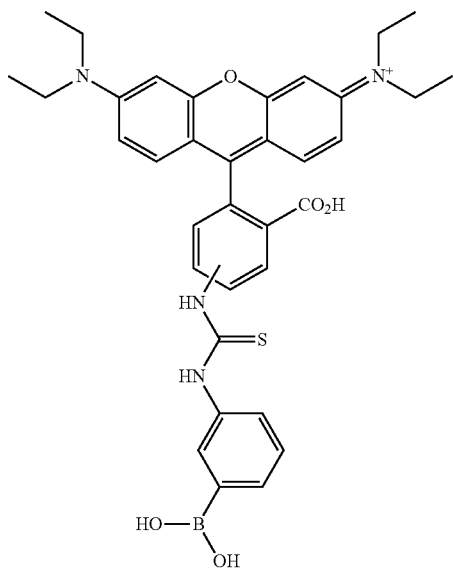
1-10
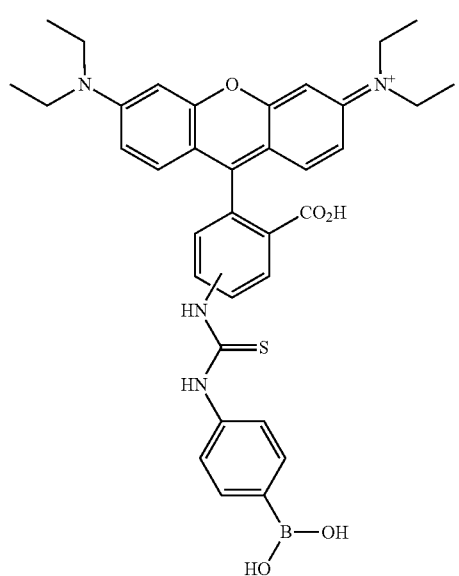
1-11
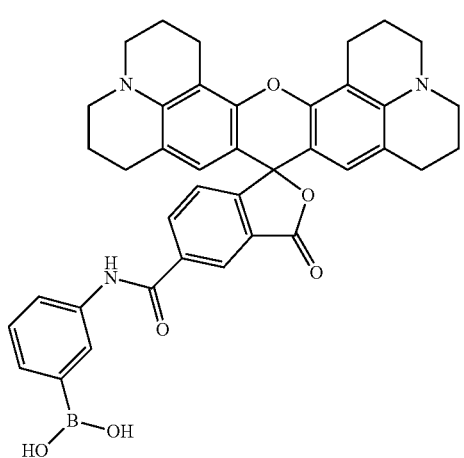
1-12
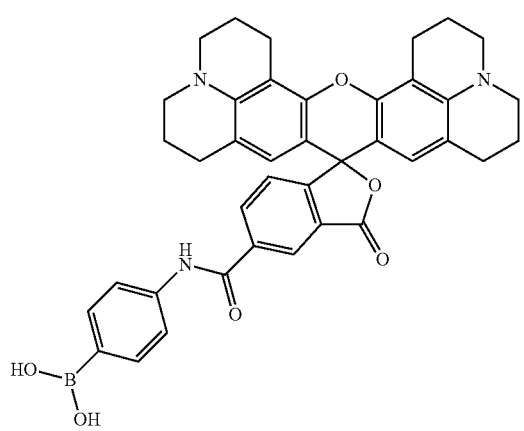
1-13
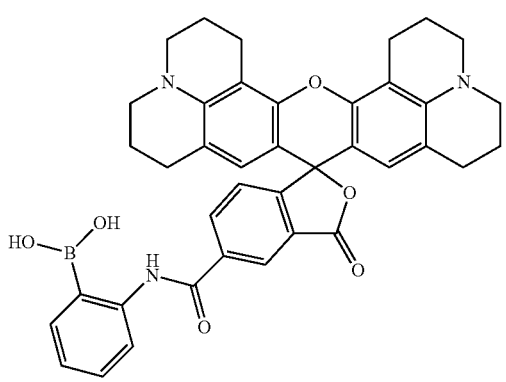

-continued
1-14
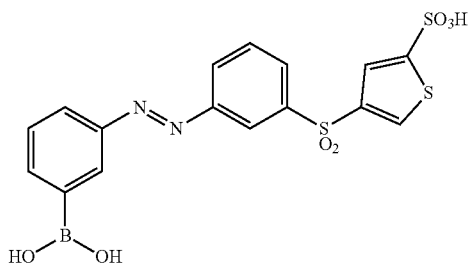
1-15
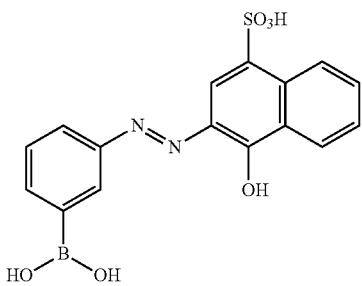
1-16
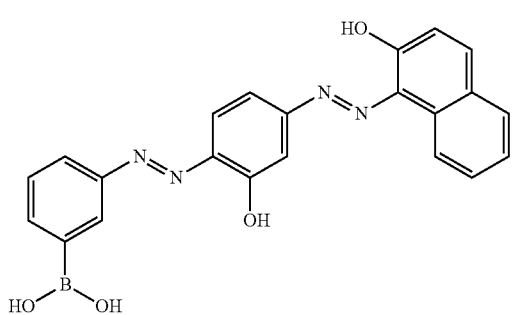
1-17
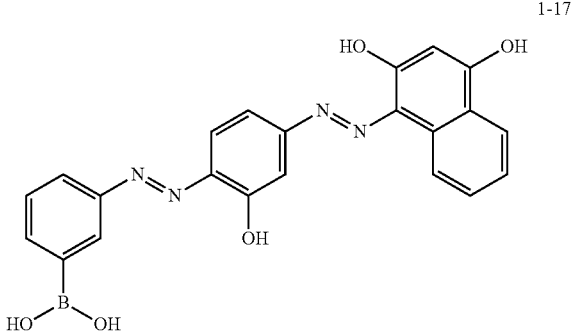
1-18
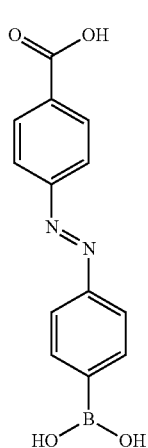
1-19
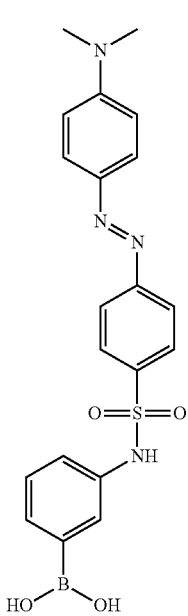
1-20
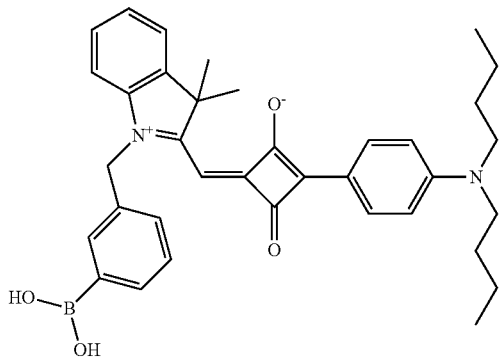
1-21
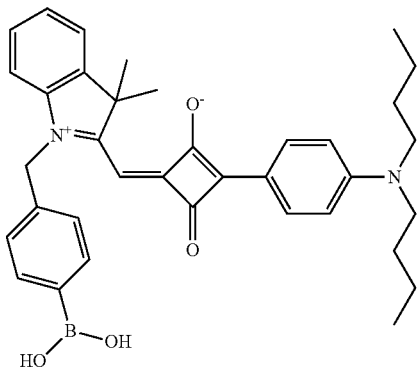

-continued
1-22
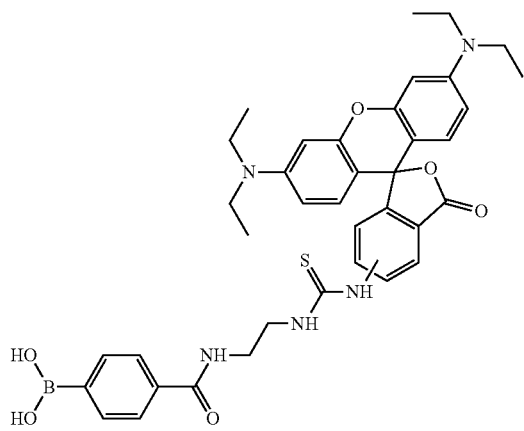
1-23
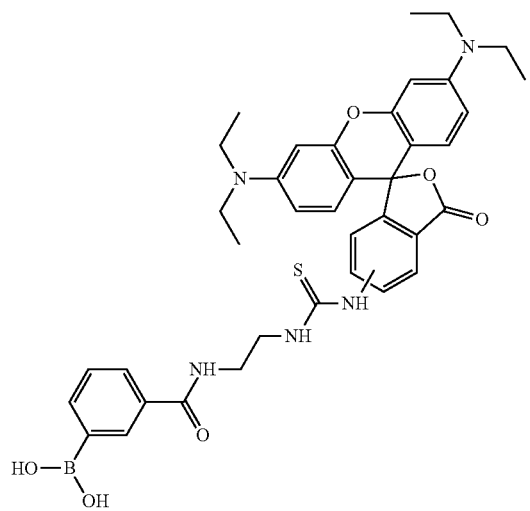
1-24
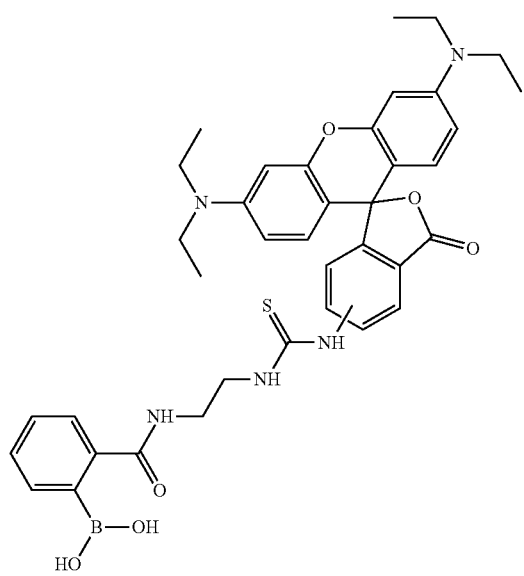
1-25
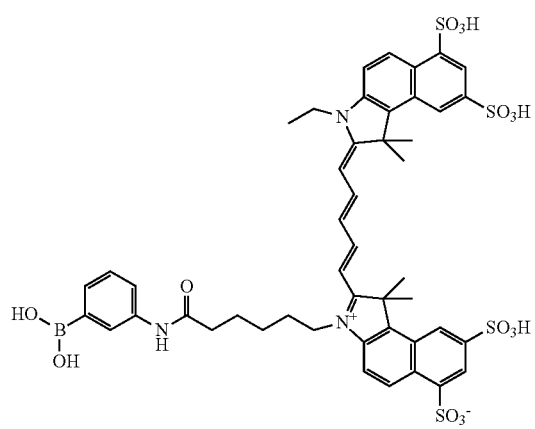
1-26
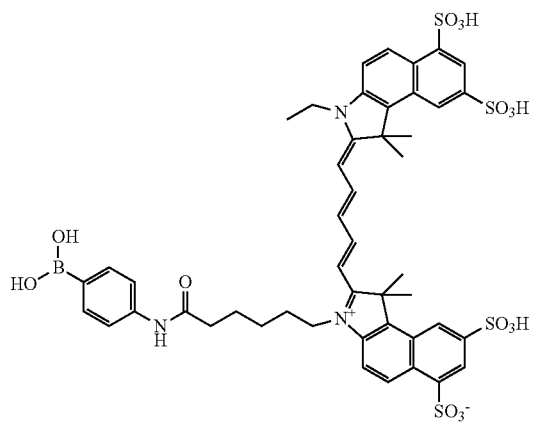
1-27
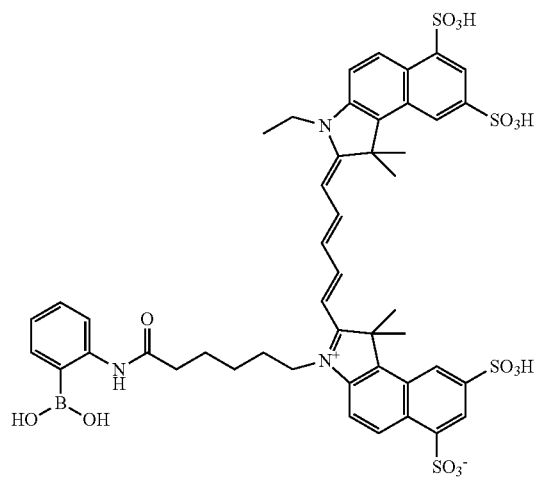

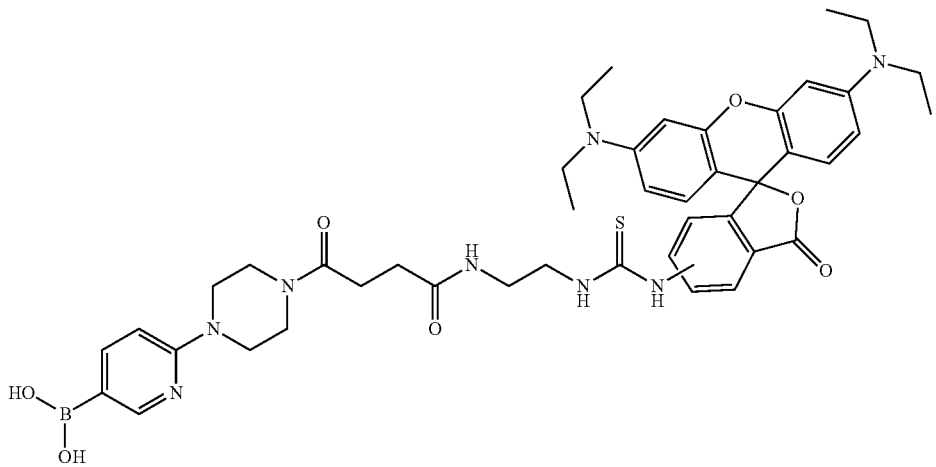

1-28

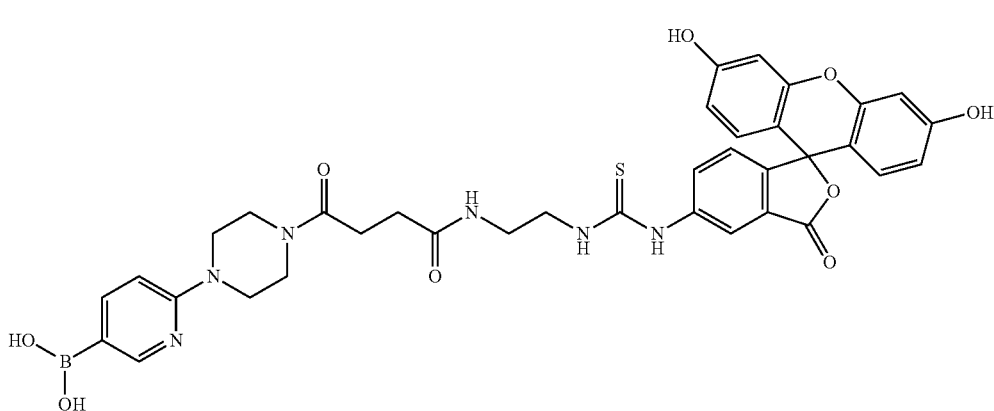

1-29

The amount of the boronic acid-containing dye used may be adjusted as appropriate depending on the molar extinction coefficient of Dye, the polyvinyl alcohol used, or an application area of the polymer dye. The amount may be such that the signal of the color intensity or the fluorescence intensity of the polymer dye on the base material can be determined or measured by visual observation or a measuring instrument such as a reflection densitometer or a fluorescence spectrophotometer.

In the method for producing the polymer dye in the present embodiment, a coupling agent containing a hydrocarbon chain or aromatic molecule having a boronic acid may be further used for coupling to part of a side chain of the polymer to produce the polymer dye. Examples of the coupling agent are presented below as 2-1 to 2-32.

In the case where the polymer dye of the present embodiment is used in a structure for detecting hydrogen peroxide in a third embodiment of the present invention, it is preferable to use a highly hydrophobic polymer dye as a polymer dye that can easily hydrophobically interact with a base material in order to bond the polymer dye to the base material. Specifically, $R^1$ in the structural formula 2 is preferably a hydrocarbon group or substituted or unsubstituted aromatic group having a partition coefficient (ClogP value) of 2 or more. Here, the ClogP value is an index of the hydrophobicity of a molecule. The higher the hydrophobicity of the molecule, the higher the ClogP value.

Then, it is preferable to use a coupling agent which can be bonded to boron atoms and in which the hydrocarbon chain or substituted or unsubstituted aromatic group has a ClogP value of 2 or more. In is preferable that the hydrocarbon chain or substituted or unsubstituted aromatic group having a ClogP value of 2 or more have a coupling structure in which it is coupled by a boric ester bond or which is an acetic ester structure. This is because, when the hydrocarbon chain or substituted or unsubstituted aromatic group having a ClogP value of 2 or more is coupled, the polymer dye has high hydrophobicity and tends to be bonded to a base material. The amount of the coupling agent used may be adjusted as appropriate depending on the ClogP value of the coupling agent used and the degree of saponification of the polyvinyl alcohol, and is preferably an amount corresponding to a monomer ratio of 4 mol % or more and 50 mol % or less of the polyvinyl alcohol for the following reasons. When the amount of the coupling agent used is too small, the polymer dye has low hydrophobicity and is hardly bonded to the base material. When the amount of the coupling agent used is too large, the polymer dye bonded to the base material has so high hydrophobicity that the polymer dye is hardly separated from the base material in the presence of hydrogen peroxide, and a color development property tends to be kept unchanged.

Specific examples of the coupling agent in the embodiment are presented below, but the coupling agent is not limited to the following structures.

2-1 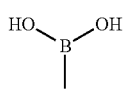
2-2 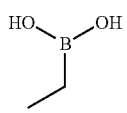
2-3 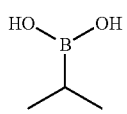
2-4 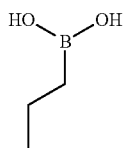
2-5 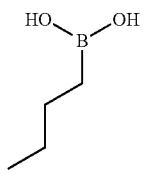
2-6 
2-7 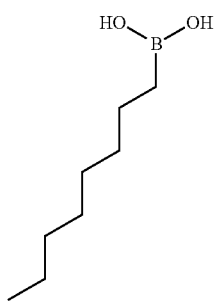
2-8 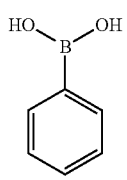
2-9 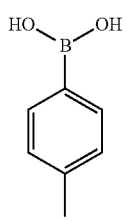
-continued
2-10 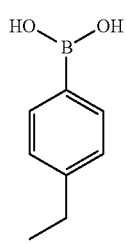
2-11 
2-12 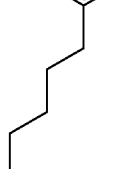
2-13 
2-14 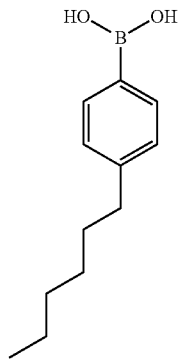

2-15 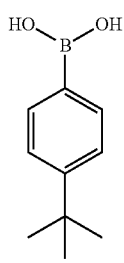
2-16 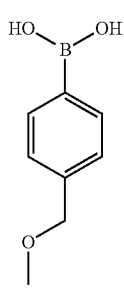
2-17 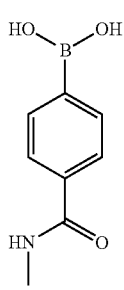
2-18 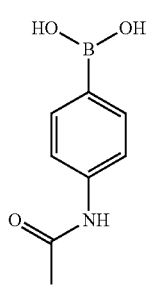
2-19 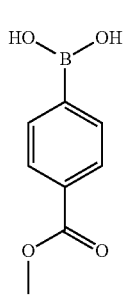
2-20 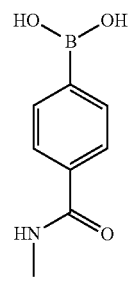
2-21 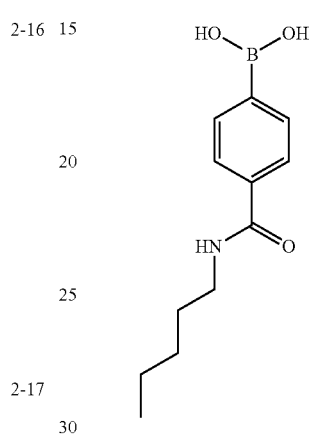
2-22 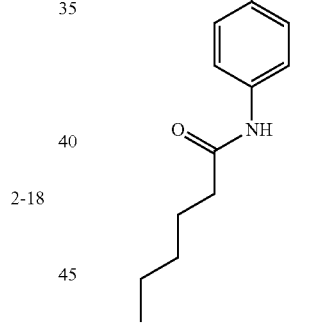
2-23 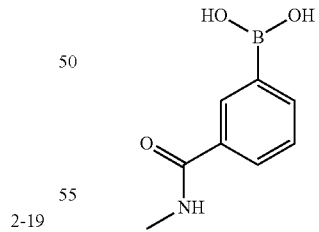
2-24 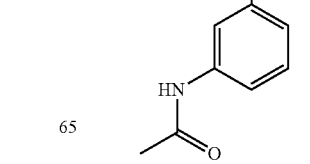

2-25 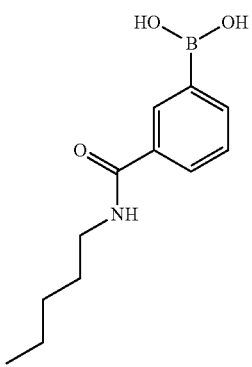

2-26 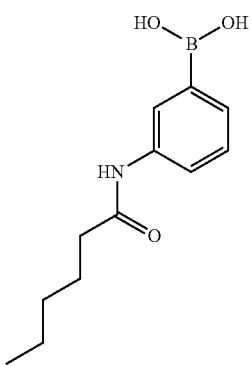

2-27 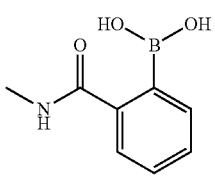

2-28 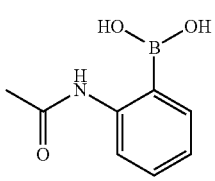

2-29 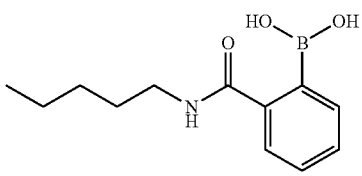

2-30 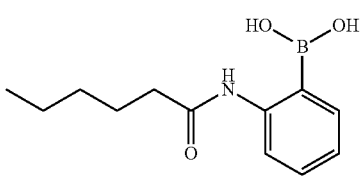

2-31 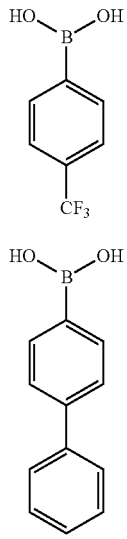

2-32 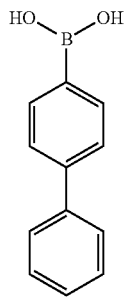

The polymer dye may be a block copolymer or a random copolymer. The block copolymer is a copolymer in which two or more blocks including a block(s) A formed of a sequence of multiple units derived from the structural formula 1 and a block(s) B formed of a sequence of multiple units derived from the structural formula 2 (or the structural formula 3) are arrayed. The random copolymer is a copolymer having a structure in which units derived from the structural formula 1 and the structural formula 2 or 3 are arrayed irregularly. Here, the unit means a unit structure corresponding to one structural formula.

The following method is a specific example of the method for producing a polymer dye in the present embodiment. Specifically, a resin such as polyvinyl alcohol is dissolved in water, a buffer solution, or an alcohol solution, and then an alcohol solution in which a dye having a boronic acid group is dissolved is added to the foregoing mixture solution, followed by drying. Subsequently, an alcohol solution in which a coupling agent containing a hydrocarbon chain or aromatic molecule having a boronic acid group is dissolved is added, followed by drying. Washing is also performed after drying if necessary, so that the polymer dye of the present invention is formed. The order of the above steps may be changed.

For example, Alexander R. Lippert et al., Acc. Chem. Res. 2011, 44, 793-804 describes a mechanism of detecting hydrogen peroxide by the polymer dye in the first embodiment of the present invention, the polymer dye for detecting hydrogen peroxide in the second embodiment of the present invention, or the structure for detecting hydrogen peroxide in the third embodiment of the present invention. In sum, an initiation reaction is the bonding of hydrogen peroxide to a boron portion of a boronic ester, and a decomposition of the carbon-boron bond occurs. In the polymer dye, the polymer dye for detecting hydrogen peroxide, or the structure for detecting hydrogen peroxide according to each embodiment of the present invention, Dye or the coupling agent is liberated from the polymer dye by hydrogen peroxide. When the amount of hydrogen peroxide is small, the amount of Dye liberated from the polymer dye is small. On the other hand, when the amount of hydrogen peroxide is large, the amount of Dye liberated from the polymer dye is large. In other words, the amount of hydrogen peroxide can be estimated by detecting the amount of Dye liberated.

Accordingly, the mechanism of detecting hydrogen peroxide by the polymer dye according to each embodiment is different from a conventional detection mechanism of demonstrating a detectable color change (absorption or luminescence) in the presence of hydrogen peroxide, and is less susceptible to environmental variations such as pH variation or influence of impurities.

Then, as the third embodiment of the present invention, provided is the structure for detecting hydrogen peroxide including a base material and a polymer dye. The base material means a solid material and may have any material properties not particularly selected as long as the material has low reactivity with hydrogen peroxide. A desirable base material is paper, felt, knitting, non-woven fabric, porous material, filter paper, or the like having an adhesive bonding layer or using cellulose, microfiber, or the like, and a paper material is preferable in terms of availability.

Regarding the detection of hydrogen peroxide by the structure for detecting hydrogen peroxide in the third embodiment of the present invention, the coupling agent contributing to the bond to the base material is liberated by hydrogen peroxide, and then the polymer dye bonded to the base material is separated from the base material. When the amount of hydrogen peroxide is small, a large amount of the polymer dye remains on the base material. On the other hand, when the amount of hydrogen peroxide is large, the amount of the polymer dye remaining on the base material is small. That is, the amount of hydrogen peroxide can be estimated by detecting the amount of the polymer dye remaining on the base material.

FIGURE illustrates an example of the structure for detecting hydrogen peroxide in the present embodiment. In FIGURE, a structure for detecting hydrogen peroxide 1 includes a polymer dye 2 and a base material 3. The structure for detecting hydrogen peroxide 1 may include a support 4 or the like as necessary. Using this, it is possible to separate the polymer dye bonded to the base material from the liberated Dye and the polymer dye separated from the base material as in paper chromatography. In the presence of hydrogen peroxide, Dye is liberated from the polymer dye and the polymer dye is separated from the base material. Reference numeral 5 indicates the liberated Dye and the separated polymer dye. The presence of hydrogen peroxide is confirmed by observing color changes of the polymer dye 2 and the base material 3 due to the liberation of Dye (such as decolorization or bleaching) or a migration of the liberated Dye 5 having transferred.

The example illustrated in FIG. 1s just an example, and the present invention should not be limited to this. In addition, the structure for detecting hydrogen peroxide 1 may be immersed in a solution containing hydrogen peroxide. The Dye eluted and the polymer dye separated by hydrogen peroxide are dissolved in the solution. The presence of hydrogen peroxide can be also confirmed by observing the amount of color development of the eluted Dye and the separated polymer dye dissolved in the solution or the color change of the polymer dye remaining in the polymer dye on the base material. Here, the amount of color development indicates a signal intensity of color intensity or fluorescence intensity.

The following method is a first production method for the structure for detecting hydrogen peroxide in the present embodiment. The production method includes a dye applying step of applying a polymer dye to a base material, the polymer dye including at least one repeating unit represented by the structural formula 1 and additionally including any one of repeating units represented by the structural formula 3 and a structural formula 4; and a coupling step of applying a paint containing a coupling agent represented by the structural formula 5 to the base material to which the polymer dye is applied. Here, $R^1$ in the structural formula 5 is the same as $R^1$ in the structural formula 2.

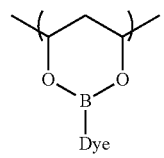

Structural Formula 1

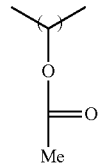

Structural Formula 3

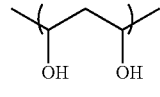

Structural Formula 4

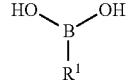

Structural Formula 5

The following method is a specific example of this production method. Specifically, a solution of a polymer dye precursor obtained by adding an alcohol solution in which a dye containing a boronic acid group is dissolved to polyvinyl alcohol and drying, the mixture is applied onto a base material, and thereafter an alcohol solution in which a hydrocarbon chain or aromatic molecule containing a boronic acid group is dissolved is applied to a sensing area.

The hydrocarbon chain or aromatic molecule containing a boronic acid group is bonded to the polyvinyl alcohol to increase the hydrophobicity of the polyvinyl alcohol, so that the polymer dye is bonded to the base material.

The following method is a second production method for the structure for detecting hydrogen peroxide in the present embodiment. The production method for the structure for detecting hydrogen peroxide includes: a resin layer applying step of applying a resin such as polyvinyl alcohol or a butyral resin having a degree of saponification of 65 mol % or more to a base material, followed by drying; a dye applying step of applying a boronic acid-containing dye represented by a structural formula 6 to the base material on which the polyvinyl alcohol or butyral resin is applied and dried, followed by drying; and a coupling step of applying a coupling agent represented by the structural formula 5 to the base material on which the boronic acid-containing dye represented by the structural formula 6 is applied and dried, followed by drying. Here, $R^1$ in the structural formula 5 is the same as $R^1$ in the structural formula 2 and Dye in the structural formula 6 is the same as Dye in the structural formula 1.

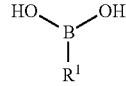

Structural Formula 5

-continued

Structural Formula 6

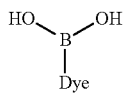

In order to increase the dye content in the polymer dye, it is preferable to produce the polymer dye on the base material as in this production method.

The following method is a specific example of this production method. Specifically, polyvinyl alcohol or a butyral resin is dissolved in water or a buffer solution, and then the solution is applied onto a sensing area on a base material. After drying, an alcohol solution in which a dye containing a boronic acid group is dissolved is applied onto the sensing area, followed by drying. Subsequently, an alcohol solution in which a hydrocarbon chain or aromatic molecule containing a boronic acid group is dissolved is applied onto the sensing area, followed by drying. Washing is performed as needed to form a structure for detecting hydrogen peroxide as a production target.

In a method using the structure for detecting hydrogen peroxide in the embodiment of the present invention, the structure may be immersed in a biological sample supplemented with an enzyme that generates hydrogen peroxide in a container so that the sensing area of the device can come into contact with the biological sample, or the biological sample may be developed on the base material and brought into contact with the sensing area by utilizing the capillary phenomenon as in paper chromatography. The enzyme may be applied in advance to the base material.

The biological sample is brought into contact with the sensing area portion on the hydrogen peroxide detection device by using the above method. Then, the amount of change in the signal intensity of the color intensity or fluorescence intensity on the sensing area portion after a lapse of a certain period of time is visually observed or measured with a measuring instrument such as a reflection densitometer or a fluorescence spectrophotometer, so that the amount of the detection target can be determined.

When the amount of the detection target is small, the amount of change on the sensing area portion is small. When the amount of the detection target is large, the amount of change on the sensing area portion is large. The amount of change may be evaluated by a developed color intensity on the sensing area or a fluorescence intensity on the sensing area with irradiation with ultraviolet rays using a ultraviolet lamp.

Further, as a fourth embodiment of the present invention, provided is a structure for detecting hydrogen peroxide including the polymer dye in the first embodiment and a base material and further including an enzyme that generates hydrogen peroxide using a detection target metabolite as a substrate. The amount of the detection target can be determined by detecting the hydrogen peroxide which is a product of an enzymatic reaction. Here, an enzyme may be set as the detection target. That is, when the structure includes a substrate for an enzyme as a detection target, the enzyme can be detected.

As enzymes for use in embodiments of the present invention, there are glucose oxidase, hexose oxidase, cholesterol oxidase, aryl-alcohol oxidase, L-gulonolactone oxidase, galactose oxidase, pyranose oxidase, L-sorbose oxidase, pyridoxine 4-oxidase, alcohol oxidase, catechol oxidase, (S)-2-hydroxy-acid oxidase, ecdysone oxidase, choline oxidase, secondary-alcohol oxidase, 4-hydroxymandelate oxidase, long-chain-alcohol oxidase, glycerol-3-phosphate oxidase, thiamin oxidase, hydroxyphytanate oxidase, nucleoside oxidase, N-acylhexosamine 0, polyvinyl-alcohol oxidase, D-arabinono-1,4-lactone oxidase, vanillyl-alcohol oxidase, nucleoside oxidase ($H_2O_2$-forming), D-mannitol oxidase, alditol oxidase, prosolanapyrone-II oxidase, paromamine 6'-oxidase, 6'''-hydroxyneomycin C oxidase, aclacinomycin-N oxidase, 5-(hydroxymethyl)furfural oxidase, 3-deoxy-α-D-manno-octulosonate 8-oxidase, (R)-mandelonitrile oxidase, aldehyde oxidase, pyruvate oxidase, oxalate oxidase, glyoxylate oxidase, indole-3-acetaldehyde oxidase, pyridoxal oxidase, aryl-aldehyde oxidase, 4-hydroxyphenylpyruvate oxidase, abscisic aldehyde oxidase, (methyl)glyoxal oxidase, coproporphyrinogen oxidase, protoporphyrinogen oxidase, bilirubin oxidase, acyl-CoA oxidase, dihydrouracil oxidase, tetrahydroberberine oxidase, secologanin synthase, tryptophan α,β-oxidase, pyrroloquinoline-quinone synthase, L-galactonolactone oxidase, albonoursin synthase, aclacinomycin-A oxidase, coproporphyrinogen III oxidase (coproporphyrin-forming), D-aspartate oxidase, L-amino-acid oxidase, D-amino-acid oxidase, amine oxidase, pyridoxal 5'-phosphate synthase, D-glutamate oxidase, ethanolamine oxidase, putrescine oxidase, L-glutamate oxidase, cyclohexylamine oxidase, protein-lysine 6-oxidase, L-lysine oxidase, D-glutamate(D-aspartate) oxidase, L-aspartate oxidase, glycine oxidase, L-lysine 6-oxidase, primary-amine oxidase, diamine oxidase, 7-chloro-L-tryptophan oxidase, pseudooxynicotine oxidase, L-arginine oxidase, sarcosine oxidase, N-methyl-L-amino-acid oxidase, $N^6$-methyl-lysine oxidase, (S)-6-hydroxynicotine oxidase, (R)-6-hydroxynicotine oxidase, L-pipecolate oxidase, dimethylglycine oxidase, dihydrobenzophenanthridine oxidase, N'-acetylpolyamine oxidase, polyamine oxidase (propane-1,3-diamine-forming), $N^8$-acetyl spermidine oxidase (propane-1,3-diamine-forming), spermine oxidase, non-specific polyamine oxidase, L-saccharopine oxidase, 4-methylaminobutanoate oxidase (formaldehyde-forming), N-alkylglycine oxidase, 4-methylaminobutanoate oxidase (methylamine-forming), coenzyme F420H2 oxidase, glyphosate oxidoreductase, NAD(P)H oxidase ($H_2O_2$-forming), NAD(P)H oxidase ($H_2O$-forming), NADH oxidase ($H_2O_2$-forming), NADH oxidase ($H_2O$-forming), renalase, nitroalkane oxidase, acetylindoxyl oxidase, factor-independent urate hydroxylase, 3-aci-nitropropanoate oxidase, hydroxylamine oxidase (cytochrome), sulfite oxidase, thiol oxidase, glutathione oxidase, methanethiol oxidase, prenylcysteine oxidase, farnesylcysteine lyase, cytochrome-c oxidase, laccase, L-ascorbate oxidase, o-aminophenol oxidase, 3-hydroxyanthranilate oxidase, rifamycin-B oxidase, photosystem II, ubiquinol oxidase (Httransporting), ubiquinol oxidase (non-electrogenic), menaquinol oxidase (Httransporting), caldariellaquinol oxidase (Ht transporting), ubiquinol oxidase (electrogenic, non Httransporting), grixazone synthase, dihydrophenazinedicarboxylate synthase, ferroxidase, bacterial non-heme ferritin, pteridine oxidase, xanthine oxidase, 6-hydroxynicotinate dehydrogenase, juglone 3-hydroxylase, isopenicillin-N synthase, columbamine oxidase, reticuline oxidase, sulochrin oxidase [(+)-bisdechlorogeodin-forming], (sulochrin oxidase [(−)-bisdechlorogeodin-forming], aureusidin synthase, tetrahydrocannabinolic acid synthase, cannabidiolic acid synthase, superoxide dismutase, superoxide reductase, NADH peroxidase, NADPH peroxidase, fatty-acid peroxidase, cytochrome-c peroxidase, catalase, peroxidase, iodide peroxidase, glutathione peroxidase, chloride peroxidase, L-ascorbate peroxidase, phospholipid-hydroperoxide glutathione peroxidase, manganese peroxidase, lignin peroxidase, peroxiredoxin, versatile peroxidase, glutathione amide-dependent peroxidase, bromide peroxidase, dye decolorizing peroxidase, prostamide/prostaglandin F2a synthase, catalase-peroxidase, hydroperoxy fatty acid reductase, (S)-2-hydroxypropylphosphonic acid epoxidase, fructosyl-amino acid oxidase, lactate oxidase, L-arginine oxidase, L-histidine oxidase, and L-cysteine oxidase. The enzymes usable in combination with the present invention are not limited to the enzymes listed above.

The detection target in the present embodiment may be a biomarker concerning a disease or a physical condition of a living body, a degree of stress applied to the living body, or the like. For example, the detection target may be glucose, uric acid, cholesterol, creatinine, or the like, but the detection target in the present embodiment of the present invention is not limited to the substances listed above. It is preferable that the detection target be one contained in urine, blood, sweat, tears, or the like.

The biological samples in the embodiment of the present invention are urine, blood, sweat, tears, mucus, liquid samples based on them, dilutions or concentrates thereof each obtained by increasing or decreasing the water content, and the like. For a detection target considered to be contained in any of these samples, the amount or concentration of the detection target metabolite in the biological sample can be measured by bringing the biological sample into contact with the enzyme and the hydrogen peroxide detection device.

Using the structure for detecting hydrogen peroxide according to the present embodiment, it is possible to provide a detection kit for hydrogen peroxide or a metabolite in a biological sample. In such a detection kit, at least a polymer dye only has to be immobilized on a base material, and the polymer dye may be immobilized on the base material on a support. When a biological sample considered to contain hydrogen peroxide is directly dropped onto the structure, the amount or concentration of the hydrogen peroxide can be measured. In addition, the kit may be provided with a separate container for immersing the structure in a biological sample. When the separate container is provided, the biological sample can be uniformly permeated into the structure. An enzyme and an aqueous solution of the enzyme may be put in the separate container in advance. At the same time as addition of a biological sample to the container, the structure can be immersed. Instead, after hydrogen peroxide is generated with a lapse of a certain period of time from addition of a biological sample to the container, the structure may be also immersed.

The detection kit may include a color chart representing hue, lightness, and saturation to check a color (fluorescence) change of the structure depending on the amount or concentration of the hydrogen peroxide or metabolite. The color chart may be printed on a separate body such as a paper sheet or plastic plate. The amount or concentration of the hydrogen peroxide or metabolite can be also determined semi-quantitatively by visually comparing the post-change color of the structure with the color chart.

EXAMPLES

Hereinafter, the present invention will be described in more details by using examples, but the present invention should not be limited to these examples as long as the scope of the present invention is not exceeded.

<Identification of Dye>

Dyes synthesized as described below were identified by using the following analysis methods:

Maldi-TOF mass spectrometry: Maldi-TOF MS (autoflex; manufactured by Bruker Daltonics); and LC/MS mass spectrometry: LC (Agilent 1200 series; manufactured by Agilent Technologies) and MS (LTQ-Orbitrap XL (FT-MS); manufactured by Thermo Fisher Scientific). Here, as an ionization method in the LC/MS mass spectrometry, an atmospheric pressure chemical ionization method (APCI) was used.

(Production Example 1) Synthesis of Boronic Acid Dye 1-4

To 5 mL of N,N-dimethylformamide, fluorescein isothiocyanate, 50 mg of isomer I (manufactured by Sigma Aldrich), 13 mg of 3-aminophenylboronic acid monohydrate, and 1 mL of triethylamine were added, and the mixture was stirred overnight at room temperature. After the solvent was distilled off, the product was purified by silica gel column chromatography to obtain an orange solid. It was confirmed by the Maldi-TOF mass spectrometry that the obtained dye had the desired structure. The result of the Maldi-TOF mass spectrometry is as follows. m/z=527.25 $[M+H]^+$ (Production Example 2) Synthesis of Boronic Acid Dye 1-9

To 3 mL of N,N-dimethylformamide, 10 mg of rhodamine B isothiocyanate (manufactured by Sigma Aldrich), 2.5 mg of 3-aminophenylboronic acid monohydrate, and 0.5 mL of triethylamine were added, and the mixture was stirred overnight at room temperature. After the solvent was distilled off, the product was purified by silica gel column chromatography to obtain a red solid. It was confirmed by the Maldi-TOF mass spectrometry that the obtained dye had the desired structure. The result of the Maldi-TOF mass spectrometry is as follows. m/z=637.60 $[M+H]^+$ (Production Example 3) Synthesis of Boronic Acid Dye 1-11

To 1 mL of N,N-dimethylformamide, 2 mg of 5-carboxy-X-rhodamine N-succinimidyl ester (manufactured by Sigma Aldrich), 0.32 mL of a N,N-dimethylformamide solution of 10 mM 3-aminophenylboronic acid monohydrate, and 0.1 mL of triethylamine were added, and the mixture was stirred overnight at room temperature. Then, a red solid was obtained by distilling off the solvent. It was confirmed by the Maldi-TOF mass spectrometry that the obtained dye had the desired structure. The result of the Maldi-TOF mass spectrometry is as follows. m/z=654.56 $[M+H]^+$ (Production Example 4) Synthesis of Boronic Acid Dye 1-22

To 5 mL of N,N-dimethylformamide, 10 mg of a compound (A) synthesized in reference to Chemistry-An Asian Journal 2008, 3(7), pp. 1134-1139, 20 mg of rhodamine B isothiocyanate (manufactured by Sigma Aldrich), and 1 mL of triethylamine were added, and the mixture was stirred overnight at room temperature. Then, a red solid was obtained by distilling off the solvent. It was confirmed by the Maldi-TOF mass spectrometry that the obtained dye had the desired structure. The result of the Maldi-TOF mass spectrometry is as follows. m/z=708.67 $[M+H]^+$

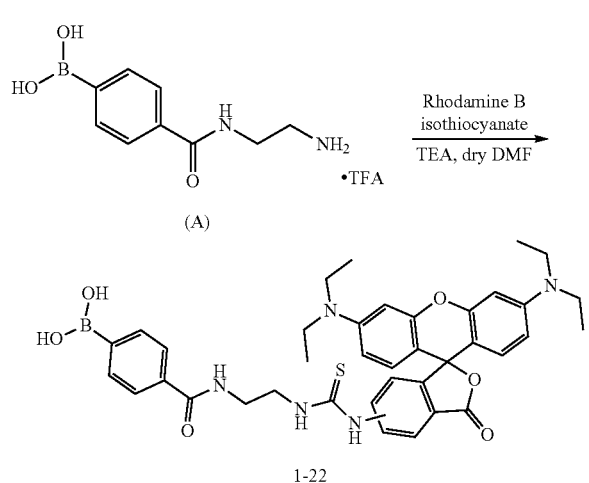

(A)

1-22

(Production Example 5) Synthesis of Boronic Acid Dye 1-25

To 0.1 mL of N,N-dimethylformamide, 90 nmol of Cy5.5 mono-NETS ester (manufactured by GE Healthcare), 90 μL of an aqueous solution of 1 mM 3-aminophenylboronic acid monohydrate, and 0.1 mL of triethylamine were added, and the mixture was stirred overnight at room temperature. Then, a blue solid was obtained by distilling off the solvent. It was confirmed by the LC/MS mass spectrometry that the obtained dye had the desired structure. The result of the LC/MS mass spectrometry is as follows. m/z=1037.33 [M+H]$^+$ (Production Example 6) Synthesis of Boronic Acid Dye 1-28 (Synthesis of Compound (C))

To 20 mL of N,N-dimethylformamide, 126 mg of a compound (B) synthesized in reference to Proc Natl Acad Sci USA 2016, 113(15), pp. E2104-E2113, 100 mg of 6-(1-piperazinyl)pyridin-3-boronic acid pinacol ester (manufactured by Sigma Aldrich), 207 mg of water-soluble carbodiimide, 120 mg of HBTU, and 1 mL of triethylamine were added, and the mixture was stirred overnight at room temperature. After the solvent was distilled off, the product was purified by silica gel column chromatography to obtain a white solid.

Synthesis of Compound (D)

To 6 mL of tetrahydrofuran, 37 mg of the compound (C), 75 mg of sodium periodate, and 0.5 mL of 2N hydrochloric acid were added, the mixture was stirred over night at room temperature, and then the solvent was distilled off. After isopropanol was added to the obtained solid, the solution was filtered. The solvent of the obtained filtrate was distilled off, followed by addition of 1 mL of trifluoroacetic acid and 1 mL of methanol and stirring over night at room temperature. Then, a white solid was obtained by distilling off the solvent.

Synthesis of Boronic Acid Dye 1-28

To 2 mL of N,N-dimethylformamide, 10 mg of the compound (D), 12 mg of rhodamine B isothiocyanate (manufactured by Sigma Aldrich), and 0.2 mL of triethylamine were added, and the mixture was stirred over night at room temperature. After the solvent was distilled off, 20 mL of chloroform and magnesium sulfate were added. The solution was filtered, and the solid on the filter paper was washed with chloroform. Then, after methanol was added to this solid, the solution was filtered. After the solvent of the obtained filtrate was distilled off and ethanol and isopropanol were added, the solution was again filtered. Then, a red solid was obtained by distilling off the solvent of the obtained filtrate. It was confirmed by the Maldi-TOF mass spectrometry that the obtained dye had the desired structure. The result of the Maldi-TOF mass spectrometry is as follows. m/z=849.44 [M+H]$^+$

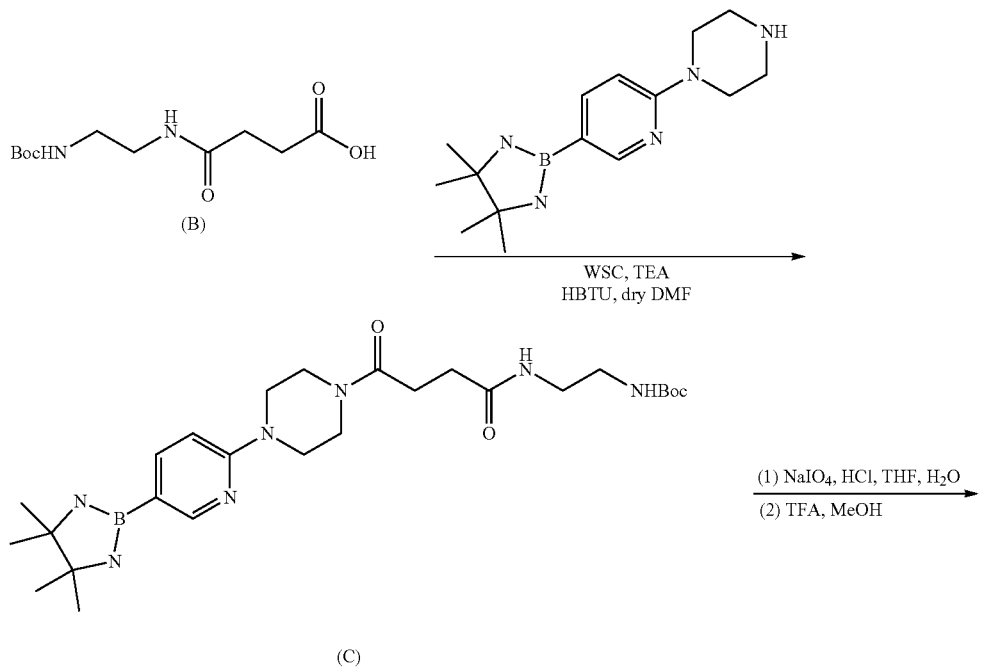

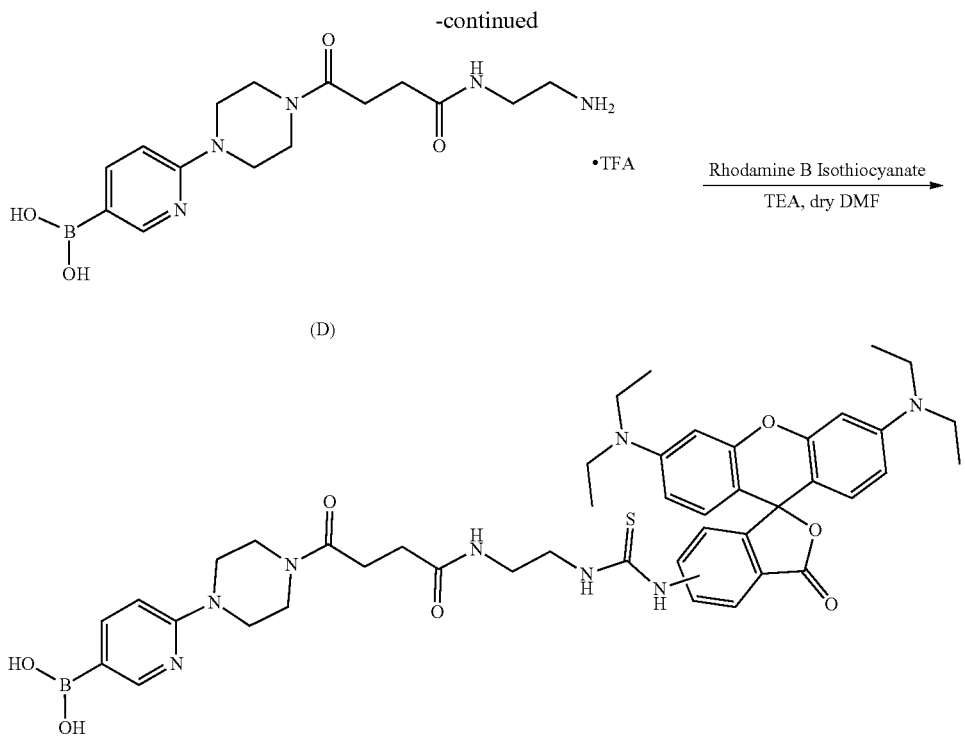

(Production Example 7) Synthesis of Coupling Agent 2-26

To 30 mL of N,N-dimethylformamide, 2.8 g of 3-aminophenylboronic acid monohydrate and 5 mL of triethylamine were added, thereafter 20 mL+ of a N,N-dimethylformamide solution containing 2.1 mg of hexanoyl chloride was added dropwise, and the mixture was stirred over night at room temperature. After the solvent was distilled off, the product was purified by silica gel column chromatography to obtain a white solid. It was confirmed by the Maldi-TOF mass spectrometry that the obtained dye had the desired structure. The result of the Maldi-TOF mass spectrometry is as follows. m/z=236.10 [M+H]$^+$ Production of Sample Paper 1

An aqueous solution (10 mg/mL, 1 μL) of polyvinyl alcohol having a degree of saponification of 86-90 mol % (VP-18: manufactured by JAPAN VAM & POVAL CO., LTD.) was applied onto a filter paper in 4 mm×30 mm (manufactured by Advantec, No. 5B) and was dried. Here, the degree of saponification is a value measured in accordance with the method of JIS-K6726. Then, a methanol solution (0.3 mM, 1 μL) of the boronic acid dye 1-22 was added to the polyvinyl alcohol-applied portion and dried. Subsequently, a methanol solution (20 mM, 1 μL) of the compound 2-26 as a coupling agent was applied to that portion and dried, followed by washing with methanol to obtain sample paper 1.

Production of Sample Paper 2

Sample paper 2 was produced in the same method as the production of the sample paper 1 except that the boronic acid dye was changed to 1-4.

Production of Sample Paper 3

Sample paper 3 was produced in the same method as the production of the sample paper 1 except that the boronic acid dye was changed to 1-9.

Production of Sample Paper 4

Sample paper 4 was produced in the same method as the production of the sample paper 1 except that the boronic acid dye was changed to 1-11.

Production of Sample Paper 5

Sample paper 5 was produced in the same method as the production of the sample paper 1 except that the boronic acid dye was changed to 1-25.

Production of Sample Paper 6

Sample paper 6 was produced in the same method as the production of the sample paper 1 except that the boronic acid dye was changed to 1-28.

Production of Sample Paper 7

Sample paper 7 was produced in the same method as the production of the sample paper 1 except that the coupling agent was changed to the compound 2-7 (manufactured by Tokyo Chemical Industry Co., Ltd.).

Production of Sample Paper 8

Sample paper 8 was produced in the same method as the production of the sample paper 1 except that the coupling agent was changed to the compound 2-8 (manufactured by Tokyo Chemical Industry Co., Ltd.).

Production of Sample Paper 9

Sample paper 9 was produced in the same method as the production of the sample paper 1 except that the coupling agent was changed to the compound 2-14 (manufactured by Tokyo Chemical Industry Co., Ltd.).

Production of Sample Paper 10

Sample paper 10 was produced in the same method as the production of the sample paper 1 except that the polyvinyl alcohol was changed to polyvinyl alcohol having a degree of saponification of 98-99 mol % (VF-17: manufactured by JAPAN VAM & POVAL CO., LTD.).

Production of Sample Paper 11

Sample paper 11 was produced in the same method as the production of the sample paper 1 except that the polyvinyl alcohol was changed to polyvinyl alcohol having a degree of saponification of 95-97 mol % (VM-17: manufactured by JAPAN VAM & POVAL CO., LTD.).

Production of Sample Paper 12

Sample paper 12 was produced in the same method as the production of the sample paper 1 except that the polyvinyl alcohol was changed to polyvinyl alcohol having a degree of saponification of 70-74 mol % (JR-05: manufactured by JAPAN VAM & POVAL CO., LTD.).

Production of Sample Paper 13

Sample paper 13 was produced in the same method as the production of the sample paper 1 except that the polyvinyl alcohol was changed to polyvinyl alcohol having a degree of saponification of 65 mol % (JMR-10M: manufactured by JAPAN VAM & POVAL CO., LTD.).

Production of Sample Paper 14

Sample paper 14 was produced in the same method as the production of the sample paper 1 except that the polyvinyl alcohol was changed to polyvinyl alcohol having a degree of saponification of 35 mol % (JMR-20L: manufactured by JAPAN VAM & POVAL CO., LTD.).

Production of Sample Paper 15

An aqueous solution (10 mg/mL, 1 µL) of polyvinyl alcohol having a degree of saponification of 86-90 mol % (VP-18) was applied onto a filter paper in 4 mm×30 mm (manufactured by Advantec, No. 5B) and dried. Then, a methanol solution (0.3 mM, 1 µL) of the boronic acid dye 1-22 was added to the polyvinyl alcohol-applied portion and dried, followed by washing with methanol to obtain sample paper 15.

Production of Sample Paper 16

Sample paper 16 was produced in the same method as the production of the sample paper 15 except that the polyvinyl alcohol was changed to the polyvinyl alcohol having a degree of saponification of 70-74 mol % (JR-05: manufactured by JAPAN VAM & POVAL CO., LTD.).

Production of Sample Paper 17

Sample paper 17 was produced in the same method as the production of the sample paper 15 except that the polyvinyl alcohol was changed to the polyvinyl alcohol having a degree of saponification of 65 mol % (JMR-10M: manufactured by JAPAN VAM & POVAL CO., LTD.).

Production of Sample Paper 18

Sample paper 18 was produced in the same method as the production of the sample paper 15 except that the polyvinyl alcohol was changed to the polyvinyl alcohol having a degree of saponification of 35 mol % (JMR-20L: manufactured by JAPAN VAM & POVAL CO., LTD.).

Example 1

The sample paper 1 was immersed in 1× phosphate buffered saline (200 µL) containing 5 mM hydrogen peroxide and 10% (v/v) fetal bovine serum at room temperature for 120 minutes for evaluation. Using a reflection densitometer RD-19 (manufactured by Gretag Macbeth), the optical density (hereinafter, referred to as the OD value) of the sample paper 1 was measured before and after the evaluation. Here, OD1 denotes the OD value of the sample paper before the evaluation and OD2 denotes the OD value of the sample paper after the evaluation. In accordance with formula (OD1−OD2)/OD1, the rate of change in the optical density before and after the evaluation was calculated. Three pieces of the sample paper 1 were produced and individually evaluated in the same way, and the average value (ΔOD) of the rates of change was calculated. Using the sample paper 1 newly produced, the average value (ΔOD0) of the rates of change in the optical density of the sample paper 1 was calculated in the same manner except that the concentration of hydrogen peroxide was changed to 0 mM. The difference between the optical densities in the presence and absence of hydrogen peroxide (ΔOD−ΔOD0) was calculated. The calculated values are presented in Table 1.

Example 2

Example 2 was carried out in the same manner as Example 1 except that the sample paper was changed to the sample paper 2.

Example 3

Example 3 was carried out in the same manner as Example 1 except that the sample paper was changed to the sample paper 3.

Example 4

Example 4 was carried out in the same manner as Example 1 except that the sample paper was changed to the sample paper 4.

Example 5

Example 5 was carried out in the same manner as Example 1 except that the sample paper was changed to the sample paper 5.

Example 6

Example 6 was carried out in the same manner as Example 1 except that the sample paper was changed to the sample paper 6.

Example 7

Example 7 was carried out in the same manner as Example 1 except that the sample paper was changed to the sample paper 7.

Example 8

Example 8 was carried out in the same manner as Example 1 except that the sample paper was changed to the sample paper 8.

Example 9

Example 9 was carried out in the same manner as Example 1 except that the sample paper was changed to the sample paper 9.

Example 10

Example 10 was carried out in the same manner as Example 1 except that the sample paper was changed to the sample paper 10.

Example 11

Example 11 was carried out in the same manner as Example 1 except that the sample paper was changed to the sample paper 11.

Example 12

Example 12 was carried out in the same manner as Example 1 except that the sample paper was changed to the sample paper 12.

Example 13

Example 13 was carried out in the same manner as Example 1 except that the sample paper was changed to the sample paper 13.

Example 14

Example 14 was carried out in the same manner as Example 1 except that the immersion time was changed to 30 minutes.

Example 15

Example 15 was carried out in the same manner as Example 14 except that the sample paper was changed to the sample paper 6.

Comparative Example 1

Comparative Example 1 was carried out in the same manner as Example 1 except that the sample paper was changed to the sample paper 14.

Comparative Example 2

Comparative Example 2 was carried out in the same manner as Example 1 except that the sample paper was changed to the sample paper 15.

Comparative Example 3

Comparative Example 3 was carried out in the same manner as Example 1 except that the sample paper was changed to the sample paper 16.

Comparative Example 4

Comparative Example 4 was carried out in the same manner as Example 1 except that the sample paper was changed to the sample paper 17.

Comparative Example 5

Comparative Example 5 was carried out in the same manner as Example 1 except that the sample paper was changed to the sample paper 18.

[Sensitivity]

For the evaluation, Examples of the present invention employed the following criteria in which A to C were determined as acceptable levels and D was determined as an unacceptable level. A larger value of $\Delta OD - \Delta OD0$ indicates that hydrogen peroxide was detected more selectively with higher sensitivity.

A: $\Delta OD - \Delta OD0$ is 0.3 or more
B: $\Delta OD - \Delta OD0$ is 0.2 or more and less than 0.3
C: $\Delta OD - \Delta OD0$ is 0.1 or more and less than 0.2
D: $\Delta OD - \Delta OD0$ is less than 0.1

Table 1 presents the average values $\Delta OD$ and $\Delta OD0$ of the rages of change in the optical density of the sample paper, a difference $\Delta OD - \Delta OD0$ between the rates of change in the optical density in the presence and absence of hydrogen peroxide, and an evaluation result in each of Examples and Comparative Examples.

TABLE 1

Evaluation Conditions and Results

| | | Evaluation Conditions | | | | Evaluation Results | | | |
|---|---|---|---|---|---|---|---|---|---|
| | Sample Paper No. | Boronic Acid Dye Type | Coupling Agent Type | Saponification Degree of Polyvinyl Alcohol (mol %) | Immersion Time (min) | $\Delta OD$ (5 mM Hydrogen Peroxide) | $\Delta OD_0$ (0 mM Hydrogen Peroxide) | $\Delta OD - \Delta OD_0$ | Sensitivity |
| Ex. 1 | 1 | 1-22 | 2-26 | 86-90 | 120 | 0.66 | 0.17 | 0.49 | A |
| Ex. 2 | 2 | 1-4 | 2-26 | 86-90 | 120 | 0.61 | — | — | A |
| Ex. 3 | 3 | 1-9 | 2-26 | 86-90 | 120 | 0.65 | 0.12 | 0.53 | A |
| Ex. 4 | 4 | 1-11 | 2-26 | 86-90 | 120 | 0.60 | 0.25 | 0.35 | A |
| Ex. 5 | 5 | 1-25 | 2-26 | 86-90 | 120 | 0.78 | 0.12 | 0.66 | A |
| Ex. 6 | 6 | 1-28 | 2-26 | 86-90 | 120 | 0.72 | 0.29 | 0.43 | A |

TABLE 1-continued

Evaluation Conditions and Results

| | Sample Paper No. | Boronic Acid Dye Type | Coupling Agent Type | Saponification Degree of Polyvinyl Alcohol (mol %) | Immersion Time (min) | ΔOD (5 mM Hydrogen Peroxide) | ΔOD$_0$ (0 mM Hydrogen Peroxide) | ΔOD − ΔOD$_0$ | Sensitivity |
|---|---|---|---|---|---|---|---|---|---|
| Ex. 7 | 7 | 1-22 | 2-7 | 86-90 | 120 | 0.75 | 0.32 | 0.43 | A |
| Ex. 8 | 8 | 1-22 | 2-8 | 86-90 | 120 | 0.76 | 0.43 | 0.33 | A |
| Ex. 9 | 9 | 1-22 | 2-14 | 86-90 | 120 | 0.31 | 0.06 | 0.25 | B |
| Ex. 10 | 10 | 1-22 | 2-26 | 98-99 | 120 | 0.53 | 0.11 | 0.42 | A |
| Ex. 11 | 11 | 1-22 | 2-26 | 95-97 | 120 | 0.56 | 0.24 | 0.32 | A |
| Ex. 12 | 12 | 1-22 | 2-26 | 70-74 | 120 | 0.76 | 0.25 | 0.51 | A |
| Ex. 13 | 13 | 1-22 | 2-26 | 65 | 120 | 0.79 | 0.54 | 0.25 | B |
| Ex. 14 | 1 | 1-22 | 2-26 | 86-90 | 30 | 0.21 | 0.01 | 0.20 | B |
| Ex. 15 | 6 | 1-28 | 2-26 | 86-90 | 30 | 0.55 | 0.12 | 0.43 | A |
| Comp. Ex. 1 | 14 | 1-22 | 2-26 | 35 | 120 | 0.64 | 0.58 | 0.06 | D |
| Comp. Ex. 2 | 15 | 1-22 | None | 86-90 | 120 | 0.81 | 0.71 | 0.10 | D |
| Comp. Ex. 3 | 16 | 1-22 | None | 70-74 | 120 | 0.77 | 0.74 | 0.03 | D |
| Comp. Ex. 4 | 17 | 1-22 | None | 65 | 120 | 0.82 | 0.74 | 0.08 | D |
| Comp. Ex. 5 | 18 | 1-22 | None | 35 | 120 | 0.76 | 0.65 | 0.11 | C |

According to the present invention, it is possible to provide a polymer dye and a structure for detecting hydrogen peroxide that are capable of detecting hydrogen peroxide present in a biological sample with high sensitivity and high selectivity.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A polymer dye comprising at least one repeating unit represented by structural formula 1 and further comprising at least one selected from the group consisting of repeating units represented by structural formulas 2 and 3:

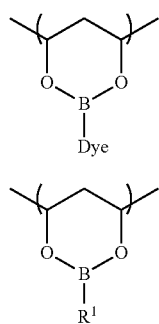

structural formula 1 structural formula 2

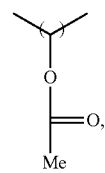

structural formula 3 wherein Dye in the structural formula 1 is a light absorbing material which contains an ionic or nonionic functional group and in which the maximum value of a molar extinction coefficient at a wavelength of 400 nm to 700 nm is $10^4$ M$^{-1}$ cm$^{-1}$ or more, and R$^1$ in the structural formula 2 is a hydrocarbon chain having 1 to 8 carbon atoms or a substituted or unsubstituted aromatic group.

2. The polymer dye according to claim 1, wherein the polymer dye comprises both of the repeating units represented by the structural formulas 2 and 3.

3. The polymer dye according to claim 1, wherein Dye in the structural formula 1 is at least one selected from the group consisting of triarylmethane dyes, azo dyes, xanthene dyes, squarylium dyes, and cyanine dyes.

* * * * *